United States Patent
Hsu et al.

(10) Patent No.: US 12,252,469 B2
(45) Date of Patent: Mar. 18, 2025

(54) CRYSTALLINE FORMS OF (E)-N-HYDROXY-3-(1-(PHENYLSULFONYL) INDOLIN-5-YL)ACRYLAMIDE

(71) Applicant: ANBOGEN THERAPEUTICS INC., Taipei (TW)

(72) Inventors: Tsu-An Hsu, Taipei (TW); Sue-Ming Chang, Taipei (TW)

(73) Assignees: Chuan Shih, Taipei (TW); ANBOGEN THERAPEUTICS INC., Taipei (TW)

( * ) Notice: Subject to any disclaimer, the term of this patent is extended or adjusted under 35 U.S.C. 154(b) by 0 days.

(21) Appl. No.: 18/802,914

(22) Filed: Aug. 13, 2024

(65) Prior Publication Data

US 2025/0011284 A1  Jan. 9, 2025

Related U.S. Application Data

(63) Continuation of application No. 18/755,310, filed on Jun. 26, 2024.

(60) Provisional application No. 63/523,377, filed on Jun. 27, 2023, provisional application No. 63/523,378, filed on Jun. 27, 2023.

(51) Int. Cl.
*C07D 209/30* (2006.01)
*A61K 9/48* (2006.01)
*A61K 31/4045* (2006.01)

(52) U.S. Cl.
CPC .......... *C07D 209/30* (2013.01); *A61K 9/4825* (2013.01); *A61K 9/4858* (2013.01); *A61K 9/4866* (2013.01); *A61K 9/4875* (2013.01); *A61K 31/4045* (2013.01)

(58) Field of Classification Search
CPC .. C07D 209/30; A61K 9/4858; A61K 9/4825; A61K 9/4875; A61K 9/4866; A61K 31/4045
See application file for complete search history.

(56) References Cited

U.S. PATENT DOCUMENTS 8,846,748 B2   9/2014   Chen et al.
11,278,523 B2 *  3/2022   Lin ........................ A61K 9/20

* cited by examiner

*Primary Examiner* — D Margaret M Seaman
(74) *Attorney, Agent, or Firm* — MUNCY, GEISSLER, OLDS & LOWE, P.C.

(57) ABSTRACT

Disclosed herein is a specific crystalline forms of (E)-N-hydroxy-3-(1-(phenylsulfonyl) indolin-5-yl) acrylamide (ABT-301), the pharmaceutical composition and capsule comprising the same, the intermediate and the medical application thereof. Said crystalline forms of ABT-301 can exhibit unexpected stability and improved pharmacokinetic properties compared to other forms or salt thereof, thereby allowing said compound more suitable for drug development and satisfying the requirements for bioavailability and drug efficacy.

23 Claims, 23 Drawing Sheets

CRYSTALLINE FORMS OF (E)-N-HYDROXY-3-(1-(PHENYLSULFONYL)INDOLIN-5-YL) ACRYLAMIDE

CROSS REFERENCE

This application is a Continuation of co-pending application Ser. No. 18/755,310, filed on Jun. 26, 2024, which claims priority to, and the benefit of, U.S. Provisional Application No. 63/523,377 and No. 63/523,378, filed on Jun. 27, 2023, the content thereof is incorporated by reference herein.

FIELD OF THE INVENTION

The present invention relates to new crystalline forms of (E)-N-hydroxy-3-(1-(phenylsulfonyl) indolin-5-yl) acrylamide (ABT-301), to pharmaceutical compositions and capsules comprising the same, and to methods of using the crystalline forms in the treatment of cancer.

BACKGROUND OF THE INVENTION

Histone deacetylases (HDACs) are a class of enzymes that regulate histone acetylation and thus regulate gene expression to inhibit tumor progression. HDACs are classified according to four categories: class I (HDAC1, 2, 3, and 8); class IIa (HDAC4, 5, 7 and 9) and class IIb (HDAC6 and 10); class III (SIRT1-7); and class IV (HDAC11). They are involved in the post-translational modifications of core histone and nonhistone proteins.

These are involved in the post-translational modifications of core histone and nonhistone proteins. U.S. Pat. No. 8,846,748 discloses certain indolyl or indolinyl hydroxamate compounds as HDAC inhibitors having potent anticancer activity. Masahiro Yoshikawa et al. indicate that HDAC inhibitors prevent fibrosis in the liver, skin and lung, U.S. Pat. No. 11,278,523 B2 discloses effect of the HDAC inhibitors on treating lung fibrosis, liver fibrosis or renal fibrosis, but most of their underlying mechanisms remain to be elucidated, and suggests that TSA, an HDAC inhibitor, induces several inhibitory factors of TGF-beta 1 signals, such as Id2 and BMP-7, in human RPTEC (Masahiro Yoshikawa et al., *J Am Soc Nephrol* 18:58-65, 2007). Maoyin Pang and Shougang Zhuang indicate that development and progression of some chronic diseases are characterized by fibrosis, including chronic kidney disease, cardic hypertrophy and idiopathic pulmonary fibrosis (Maoyin Pang and Shougang Zhuang, *The Journal of Pharmacology and Experimental Therapeutics*, Vol. 355, No. 2, pp. 266-272, 2010).

As such, HDAC inhibitors (HDACi) have emerged as a promising class of drugs for treatment of cancers. Some HDACi, such as SAHA, LBH589, PXD101, MS-275, and FK228, are being examined in clinical trials for their ability to treat various solid and hematological malignancies. On the other hand, SAHA and FK228 have been approved by the U.S. Food and Drug Administration (FDA) to apply for the treatment of cutaneous T-cell lymphoma.

Certain indolyl or indolinyl hydroxamate compounds as HDAC inhibitors are disclosed in U.S. Pat. No. 8,846,748B2. Nevertheless, the differences in various aspects between crystalline forms of said compounds have barely been discussed.

SUMMARY OF THE INVENTION

The invention is based on the discovery that certain crystalline forms of (E)-N-hydroxy-3-(1-(phenylsulfonyl) indolin-5-yl) acrylamide (ABT-301), which exhibit unexpected and improved pharmacokinetic properties.

Accordingly, the present invention provides a crystalline form of (E)-N-hydroxy-3-(1-(phenylsulfonyl) indolin-5-yl) acrylamide (ABT-301), wherein the crystalline form comprises Type A form or Type B form; wherein Type A form is characterized by an X-ray powder diffraction pattern comprising peaks at 2θ values of 9.6±0.2, 15.1±0.2, 15.7±0.2°, 16.7±0.2, 18.4±0.2, 19.0±0.2 and 20.4±0.2; and wherein Type B form is characterized by an X-ray powder diffraction pattern comprising peaks at 2θ values of 15.7±0.2, 16.6±0.2, 20.1±0.2 and 24.1±0.2°.

Further, Type A form is characterized by an X-ray powder diffraction pattern further comprising peaks at 2θ value of 10.2±0.2, 11.8±0.2, 17.4±0.2, 21.3±0.2 and 21.9±0.2.

Further, Type A form is hydrate.

Further, Type B form is characterized by an X-ray powder diffraction pattern further comprising peaks at 2θ value of 12.5±0.2° and 21.7±0.2.

Further, Type B form is anhydrate.

Further, the crystalline form provided herein has a melting point temperature of 125 to 132° C.

Further, Type A form has a TGA weight loss of 2 to 4% when heated to a temperature of 100 to 150° C.

Further, Type A form has a water uptake of 0.13 to 0.14% at 25° C./80% RH.

Further, Type B form has a TGA weight loss of 0.7 to 0.8% when heated to a temperature of 150 to 170° C.

Further, Type B form has a water uptake of 0.103 to 0.109% at 25° C./80% RH.

The present invention provides an intermediate for preparing Type A form or Type B form, wherein the intermediate is a solvate of ABT-301, and the solvate comprises IPA solvate, acetone solvate, ACN solvate, MeOH solvate, NMP solvate, THF solvate, EtOAc solvate, DMAc solvate, EtOH solvate, DCM solvate, DMSO solvate, 1-4-Dioxane solvate or MIBK solvate.

The present invention provides a pharmaceutical composition comprising the crystalline form provided herein, a surfactant and an oil.

Further, the surfactant is polysorbate 80.

Further, the oil is castor oil.

Further, the crystalline form provided herein is a HDAC inhibitor.

Further, the pharmaceutical composition is in a form of a capsule.

Further, the capsule provided herein comprises from 25 to 100 mg of said crystalline form.

Further, the pharmaceutical composition is encapsulated in a gelatin shell.

Further, the pharmaceutical composition comprises a plasticizer.

Further, the plasticizer is propylene glycol.

The present invention provides a method of treating cancer or fibrosis, comprising administering to a patient in need thereof a therapeutically effective amount of the crystalline form provided herein.

Further, according to the method of the present invention, wherein the cancer is pancreatic cancer, bladder cancer, colorectal cancer, breast cancer, prostate cancer, renal cancer, hepatocellular cancer, lung cancer, non-small cell lung cancer (NSCLC), ovarian cancer, cervix cancer, gastric cancer, esophageal cancer, neuroendocrine cancer, bone cancer, or head and neck cancer.

Further, according to the method of the present invention, wherein the fibrosis is lung fibrosis, liver fibrosis, skin fibrosis or renal fibrosis.

Accordingly, the effect of the present invention is that the specific crystalline form of ABT-301 can exhibit unexpected stability and improved pharmacokinetic properties compared to other forms or salt thereof, thereby allowing said compound more suitable for drug development and satisfying the requirements for bioavailability and drug efficacy.

BRIEF DESCRIPTION OF THE DRAWINGS

In order to make the above and other objects, features, advantages and embodiments of the present invention more obvious and understandable, the drawings are described as follows.

DETAILED DESCRIPTION OF THE INVENTION

Definition

Figure 1:
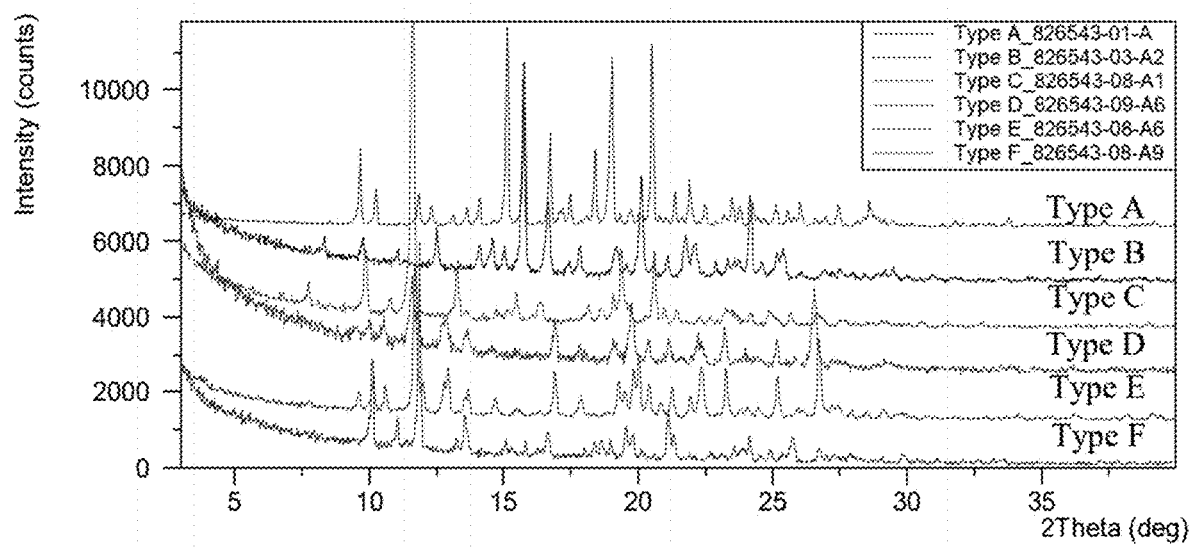
FIGS. 1 to 3 illustrate XRPD patterns overlay of a crystalline form of ABT-301 free base.

The terms used in this specification are generally within the scope of the present invention and the specific context of each term has its usual meaning in related fields. The specific terms used to describe the present invention in this specification will be described below or elsewhere in this specification, so as to help people in the industry understand the relevant description of the present invention. The same term has the same scope and meaning in the same context. In addition, there is more than one way to express the same thing; therefore, the terms discussed in this article may be replaced by alternative terms and synonyms, and whether a term is specified or discussed in this article does not have any special meaning. This article provides synonyms for certain terms, but the use of one or more synonyms does not mean that other synonyms are excluded.

As used herein, unless the context clearly indicates otherwise, "a" and "the" can also be interpreted as plural. In addition, in this specification and the scope of the attached patent application, unless otherwise stated in the context, "middle" and "inner" include "located in"; and unless otherwise stated in the context, the direction of the tip of the projectile was defined as "upper" or "lower". Furthermore, titles and subtitles may be attached to the description for easy reading, but these titles do not affect the scope of the present invention.

As used herein, the term "crystalline" may refer to having a regularly repeating arrangement of molecules or external face planes. Crystalline forms may differ with respect to thermodynamic stability, physical parameters, X-ray structure and preparation processes.

As used herein, the term "amorphous" may refer to a form of a compound, or a salt or molecular complex of a compound, that lacks long range crystalline order where the x-ray diffraction pattern lacks Bragg reflections.

As used herein, the term "solid form" may refer to a crystalline solid form or phase, including crystalline free base, crystalline salt, or a cocrystal, as well as an amorphous phase, including an amorphous dispersion.

As used herein, the term "solvate" may refer to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

As used herein, unless otherwise indicated, the term "treating" means reversing, alleviating, inhibiting the progress of, or preventing the disorder or condition to which such term applies, or one or more symptoms of such disorder or condition. The term "treatment", unless otherwise indicated, refers to the act of treating as "treating as defined immediately above.

As used herein, the term "effective amount" or "therapeutically effective amount" refers to that amount of a compound or combination of compounds that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimens to be followed, whether the compound is administered in combination with other compounds, timing of administration, the tissue to which it is administered, and the physical delivery system in which the compound is carried.

Crystalline Form of ABT-301

In an embodiment, the present invention provides a crystalline form of (E)-N-hydroxy-3-(1-(phenylsulfonyl) indolin-5-yl) acrylamide (ABT-301, represented by Formula I).

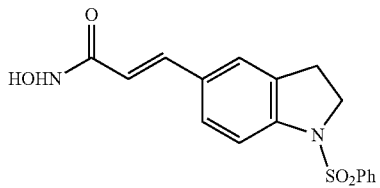

(Formula I)

ABT-301 (previously known as MPTOE028) is a novel N-hydroxyacrylamide derived HDAC inhibitor, of which the crystalline form comprises Type A form (Also simply referred to as "Type A" below) and/or Type B form (Also simply referred to as "Type B" below).

Type A form is hydrate, which is characterized by an X-ray powder diffraction pattern comprising peaks at 2θ values selected from the group consisting of 9.6±0.2, 15.1±0.2, 15.7±0.2, 16.7±0.2, 18.4±0.2, 19.0±0.2 and 20.4±0.2. Preferably, Type A form is characterized by an X-ray powder diffraction pattern comprising peaks at 2θ values of 9.6±0.2, 15.1±0.2, 15.7±0.2, 16.7±0.2, 18.4±0.2, 19.0±0.2 and 20.4±0.2. In another embodiment, Type A form is characterized by an X-ray powder diffraction pattern further comprising peaks at 2θ value selected from the group consisting of 10.2±0.2, 11.8±0.2, 17.4±0.2, 21.3±0.2 and 21.9±0.2. More preferably, Type A form is characterized by an X-ray powder diffraction pattern further comprising peaks at 2θ value of 10.2±0.2, 11.8±0.2, 17.4±0.2, 21.3±0.2 and 21.9±0.2.

Type B form is anhydrate, which is characterized by an X-ray powder diffraction pattern comprising peaks at 2θ values selected from the group consisting of 15.7±0.2, 16.6±0.2, 20.1±0.2 and 24.1±0.2. Preferably, Type B form is characterized by an X-ray powder diffraction pattern comprising peaks at 2θ values of 15.7±0.2, 16.6±0.2, 20.1±0.2 and 24.1±0.2. In another embodiment, Type B form is characterized by an X-ray powder diffraction pattern further comprising peaks at 2θ value of 12.5±0.2 and/or 21.7±0.2. More preferably, Type B form is characterized by an X-ray powder diffraction pattern further comprising peaks at 2θ value of 12.5±0.2 and 21.7±0.2.

It is known in the art that an X-ray powder diffraction (XRPD) pattern may be obtained with one or more measurement errors depending on measurement conditions (such as equipment, sample preparation or instrument used). In particular, it is generally known that intensities in an X-ray powder diffraction pattern may vary depending on measurement conditions and sample preparation. For example, persons skilled in the art of X-ray powder diffraction realize that the relative intensities of peaks may vary according to the orientation of the sample under test and based on the type and settings of the instrument used. The skilled person also realize that the position of reflections can be affected by the precise height at which the sample sits in the diffractometer, the sample's surface planarity, and the zero calibration of the diffractometer. Hence a person skilled in the art will appreciate that the diffraction pattern data presented herein is not to be construed as absolute and any crystalline form that provides a power diffraction pattern substantially the same as those disclosed herein fall within the scope of the present disclosure. For further information, see Jenkins and Snyder, *Introduction to X-Ray Powder Diffractotmetry*, John Wiley & Sons, 1996.

In an embodiment, the crystalline form provided herein has a melting point temperature of 125 to 132° C.; more particularly, said melting point temperature is, for example, 125, 125.5, 126, 126.5, 127, 127.5, 128, 128.5, 129, 129.5, 130, 130.5, 131, 131.5, or 132° C. In each of the foregoing embodiment, the melting point temperature characterizing the crystalline form of the present invention is analyzed by differential scanning calorimetry (DSC), including modulated differential scanning calorimetry or temperature-modulated differential scanning calorimetry.

In an embodiment, Type A form has a TGA weight loss of 2 to 4% when heated to a temperature of 100 to 150° C. For example, said TGA weight loss is 2, 2.5, 3, 3.5 or 4%. In an embodiment, Type B form has a TGA weight loss of 0.7 to 0.8% when heated to a temperature of 150 to 170° C. For example, said TGA weight loss is 0.7, 0.75 or 0.8%.

In an embodiment, Type A form has a water uptake of 0.13 to 0.14% at 25° C./80% RH. For example, said water uptake is 0.13, 0.135 or 0.14%. In an embodiment, Type B form has a water uptake of 0.103 to 0.109% at 25° C./80% RH. For example, said water uptake is 0.103, 0.105, 0.107 or 0.109%.

In another aspect, the present invention provides an intermediate for preparing Type A form or Type B form, wherein the intermediate is a solvate of ABT-301. In a preferable embodiment, the solvate comprises IPA solvate, acetone solvate, ACN solvate, MeOH solvate, NMP solvate, THF solvate, EtOAc solvate, DMAc solvate, EtOH solvate, DCM solvate, DMSO solvate, 1-4-Dioxane solvate or MIBK solvate. In some embodiments, the intermediate may be prepared by using Type A as a starting material, dissolving it in the different solvents and the final form was obtained from the clear solution. In some embodiments, Type A form or Type B form can be obtained from the intermediate.

PHARMACEUTICAL COMPOSITION

In an embodiment, the present invention provides a pharmaceutical composition comprising the crystalline form provided herein. More specifically, said pharmaceutical composition is a HDAC inhibitor. Where desired, the pharmaceutical compositions contain a surfactant and an oil. In some embodiments, the surfactant is polysorbate 80 and the oil is castor oil.

In some embodiments, the pharmaceutical composition comprises a plasticizer. Preferably, the plasticizer is propylene glycol. In some embodiment, the pharmaceutical composition comprises a pharmaceutically acceptable salt thereof, and one or more pharmaceutically acceptable excipients, carriers, including inert solid diluents and fillers, diluents, permeation enhancers, solubilizers, or adjuvants.

In another aspect, the present invention provides a capsule comprising said pharmaceutical composition. Preferably, the capsule is encapsulated in a gelatin shell. Further, the capsule provided herein comprises from 25 to 100 mg of the crystalline form of ABT-301; more particularly, the amount of said crystalline form is, for example, 25, 30, 35, 40, 45, 50, 55, 60, 65, 70, 75, 80, 85, 90, 95 or 100 mg. In an preferred embodiment, the capsule provided herein comprises 50 mg of the crystalline form of ABT-301.

Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil emulsion. Pharmaceutical compositions of the invention also include powder for reconstitution, powders for oral consumptions, bottles (such as powder or liquid in bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation.

METHOD OF TREATMENT

The present invention provides a method of treating cancer, comprising administering to a patient in need thereof a therapeutically effective amount of the crystalline form of ABT-301 free base.

In some embodiments, the crystalline form of ABT-301 administered is a HDAC inhibitor.

In selected embodiments, the crystalline form of ABT-301 is administered in a single dose. A single dose of the crystalline form of ABT-301 may also be used for treatment of an acute condition. In selected embodiments, the crystalline form of ABT-301 is administered in multiple doses. Dosing may be about once, twice, three times, four times, five times, six times, or more than six times per day. Preferably, the crystalline form of ABT-301 is administered once per day. Dosing may be about once a month, once every two weeks, once a week, or once every other day. In some embodiments, the duration between the first dose and last dose of the multiple doses is about 1-1.5 months. In other embodiments, the crystalline form of ABT-301 is administered one or more times. For example, the crystalline form of ABT-301 is administered once for a full course of treatment. The crystalline form of ABT-301 is administered about once per day to about 6 times per day. In another embodiment the administration of the crystalline form of ABT-301, continues for less than about 7 days. In yet another embodiment the administration continues for more than about 6, 10, 14, 28 days, two months, six months, or one year. In some cases, continuous dosing is achieved and maintained as long as necessary.

In some embodiments, the crystalline form of ABT-301 is administered by any suitable route, such as but not limited to by enteral, oral, nasal, parenteral (for example, intratumoral, intramuscular, intravenous, intraarticular, intraarterial, subcutaneous, intraperitoneal, intracerebral, intrasynovial, intrastemal, intracerebroventricular or intrathecal injection), or transmucosal administration. Preferably, the crystalline form of ABT-301 is administered by oral.

Further, according to the method of the present invention, wherein the cancer includes both solid and haematological tumours of various organs. In some embodiments, the cancer is pancreatic cancer, bladder cancer, colorectal cancer, breast cancer (such as metastatic breast cancer), prostate cancer (such as androgen-dependent and androgen-independent prostate cancer), renal cancer (such as metastatic renal cell carcinoma), hepatocellular cancer, lung cancer (such as bronchioloalveolar carcinoma (BAC), and adenocarcinoma of the lung), non-small cell lung cancer (NSCLC), ovarian cancer (such as progressive epithelial or primary peritoneal cancer), cervix cancer, gastric cancer, esophageal cancer, neuroendocrine cancer (such as metastatic neuroendocrine tumors), bone cancer, head and neck cancer (such as squamous cell carcinoma of the head and neck), melanoma, or brain tumors (such as glioma, anaplastic oligodendroglioma, adult glioblastoma multiforme, and adult anaplastic astrocytoma). Wherein the fibrosis is lung fibrosis, liver fibrosis, skin fibrosis or renal fibrosis.

Although the numerical ranges and parameters used to define the present invention are approximate values, the relevant values in the specific embodiments have been presented as accurately as possible. However, any numerical value inevitably contains standard deviations due to individual test methods. Here, "about" generally means that the actual value is within plus or minus 10%, 5%, 1%, or 0.5% of a specific value or range. Or, the term "about" means that the actual value falls within the acceptable standard error of the average value, which is determined by those with ordinary knowledge in the field to which the present invention belongs. Therefore, unless otherwise stated to the contrary, the numerical parameters disclosed in this specification and the accompanying patent application are approximate values and can be changed as required. At least these numerical parameters should be understood as the indicated significant digits and the values obtained by applying the general rounding method.

EXAMPLES

In this section, the contents of the present invention will be described in detail through the following examples. These examples are for illustration only, and those skilled in the art can easily think of various modifications and changes. As such, various embodiments of the present invention will be described in detail below, while the invention is not limited to said various embodiments listed in this specification.

Example 1

Preparation of ABT-301 Compound

ABT-301 compound can be synthesized/prepared via any suitable methods known in the art, such as the routes and methods disclosed in the U.S. Pat. No. 8,846,748 B2.

Example 2

Physical Characterization of Crystalline Forms of ABT-301

I. Polymorph Screening for ABT-301

Figure 2:
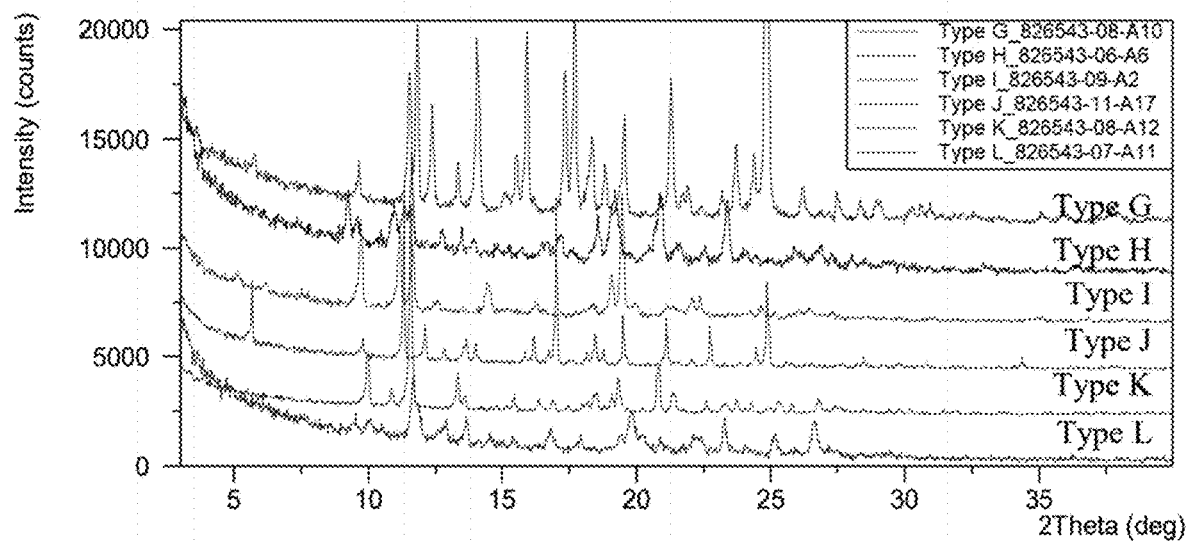
Figure 3:
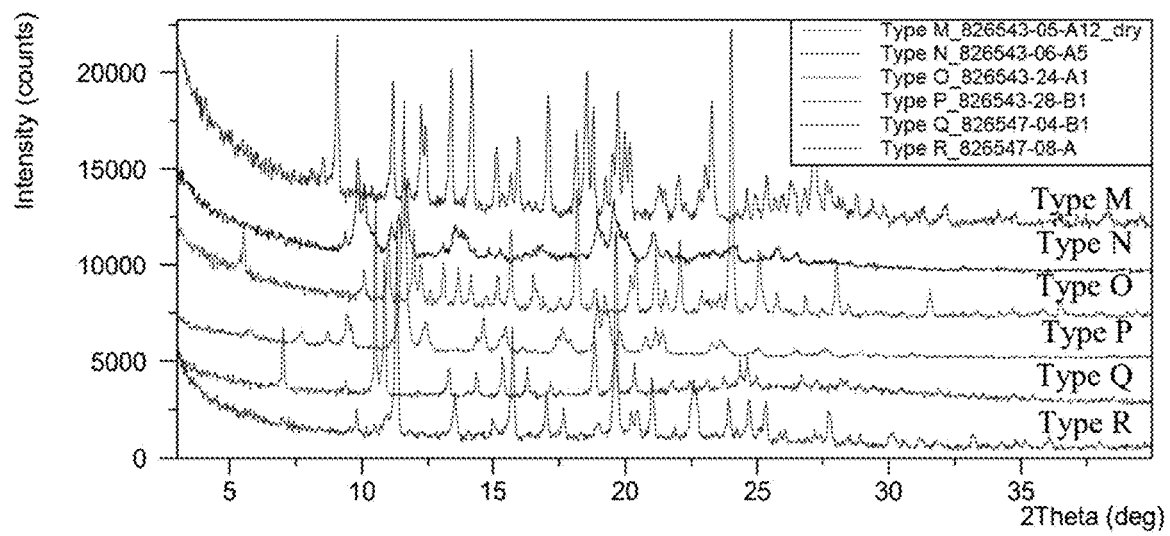

Using ABT-301 Type A (Sample name: ABT-301, CP ID: 826543-01-A) as starting material, a total of 100 polymorph screening experiments were performed, using methods of vapor-solution diffusion, vapor-solid diffusion, slow evaporation, slurry (RT and 50° C.), temperature cycling, slow cooling, anti-solvent addition and grinding. Based on the characterization results and further experiments, a total of eighteen polymorphs were obtained, which were characterized by X-ray powder diffraction (XRPD), thermo gravimetric analysis (TGA), differential scanning calorimetry (DSC) and 1H solution nuclear magnetic resonance (1H NMR). Type A was postulated to be a hydrate, Type B was postulated to be an anhydrate, Type C/D/E/F/G/H/I/J/K/L/M/N/O/R were postulated to be solvates, and Type P/Q were unidentified due to form conversion after drying. The characterization results of polymorphs were summarized in Table 1 and the XRPD results were displayed from FIG. 1 to FIG. 3.

TABLE 1

| Form | Sample ID | TGA weight loss (%, ° C.) | DSC endotherm (° C., peak) | Postulated form |
| --- | --- | --- | --- | --- |
| Type A | 826543-01-A | 3.77 (150) | 118.7, 125.5, 166.1* | Hydrate |
| Type B | 826543-08-A2 | 0.94 (150) | 166.0* | Anhydrate |
| Type C | 826543-08-A1 | 5.07 (115) 3.46 (140) | 117.4, 126.4*, 159,7* | IPA solvate |
| Type D | 826543-09-A6 | 7.42 (130) | 114.8, 144.14, 157.2* | Acetone solvate |
| Type E | 826543-08-A6 | 2.21 (120) 3.37 (140) | 120.7, 131.6, 142.4*, 159.5* | ACN solvate |
| Type F | 826543-08-A9 | 4.64 (130) | 117.8, 136.5, 146.0* | McOH solvate |
| Type G | 826543-08-A10 | 12.45 (145) | 148.0, 156,0* | NMP solvate |
| Type H | 826543-06-A6 | 11.75 (150) | 102.1, 118.6*, 158.4* | THF solvate |
| Type I | 826543-09-A2 | 6.88 (120) 2.06 (150) | 118.6, 123.7, 160.5* | EtOAc solvate |
| Type J | 826543-11-A17 | 12.16 (130) | 136.6, 138.4, 145.0* | DMAc solvate |
| Type K | 826543-08-A12 | 4.53 (120) 3.19 (140) | 120.7, 140.3, 135.4*, 143.7*, 156.8* | EtOH solvate |
| Type L | 826543-07-A11 | 8.19 (140) | 117.4, 144.0*, 154.2* | DCM solvate |
| Type M | 826543-05-A12_dry | 5.41 (130) | 104.7, 142.8* | DMSO solvate |
| Type N | 826543-06-A5 | 6.07 (120) | 91.6. 109.3, 148.1* | 1,4-Dioxane solvate |
| Type O | 826543-24-A1 | 21.84 (100) | 82.6, 84.5, 163.2* | MIBK solvate |
| Type P | 826543-28-B1 | The sample converted to Type A after dried at RT overnight. | | |
| Type Q | 826547-04-B1 | The sample converted to Type M after dried at RT in open air for 8 days and under vacuum for 16.5 hours | | |
| Type R | 826547-08-A | 5.81 (130) | 143.5* | DMSO solvate |

*Exotherm.

TABLE 2

| Solvent | Solubility (mg/mL) | Solvent | Solubility (mg/mL) |
| --- | --- | --- | --- |
| MeOH | 20.0 < S < 40.0 | 1,4-Dioxane | 21.0 < S < 42.0 |
| EtOH | 5.5 < S < 11.0 | ACN | 9.5 < S < 19.0 |
| IPA | 2.0 < S < 5.0 | CHCl$_3$ | S < 1.0 |
| Acetone | S > 40.0 | DCM | 1.0 < S < 2.0 |
| MIBK | 2.0 < S < 5.0 | n-Heptane | S < 1.0 |
| EtOAc | 2.0 < S < 5.0 | Toluene | S < 1.0 |
| IPAc | S < 1.1 | DMAc | S > 40.0 |
| MTBE | S < 1.0 | DMSO | S > 40.0 |
| THE | S > 44.0 | NMP | S > 40.0 |
| 2-MeTHF | 2.0 < S < 5.0 | H$_2$O | S < 1.0 |

Figure 7:
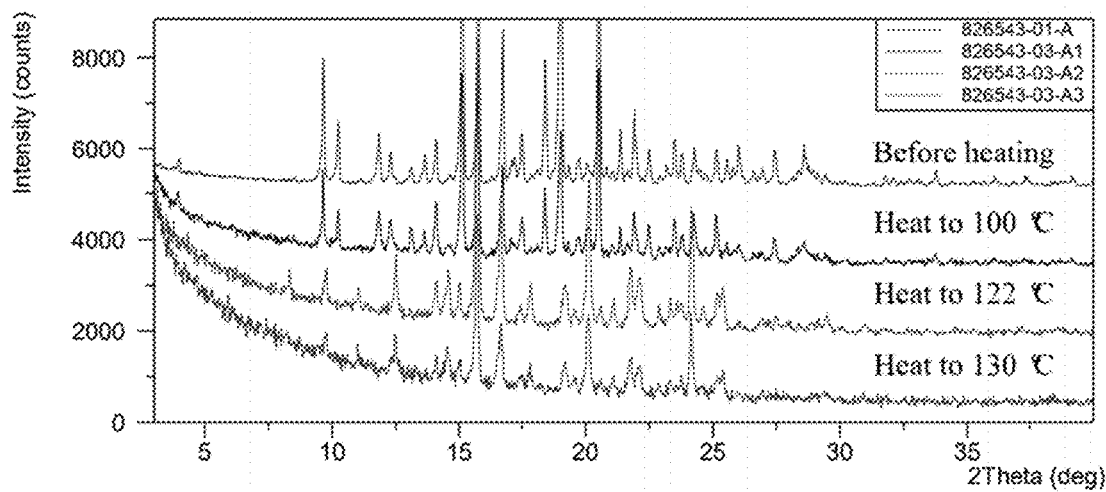
FIG. 7 illustrates a XRPD pattern overlay of ABT-301 Type A before and after heating.
Figure 8:
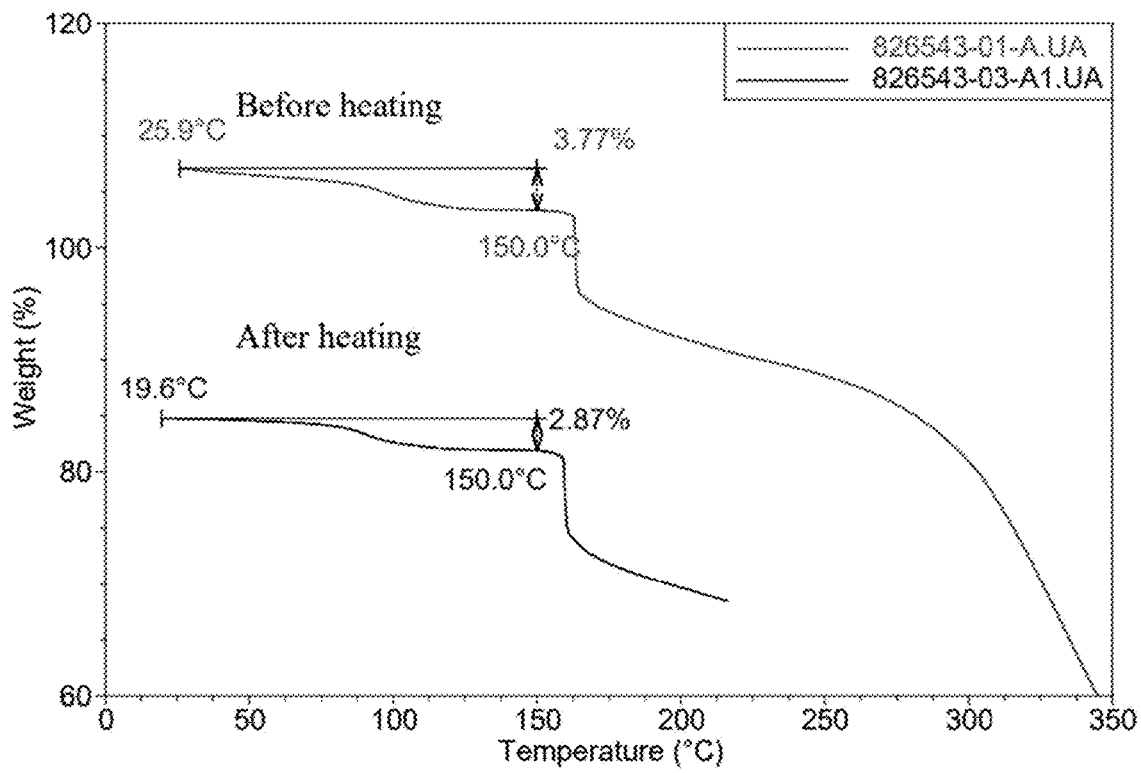
FIG. 8 illustrates TGA overlay of ABT-301 Type A before and after heating
Figure 9:
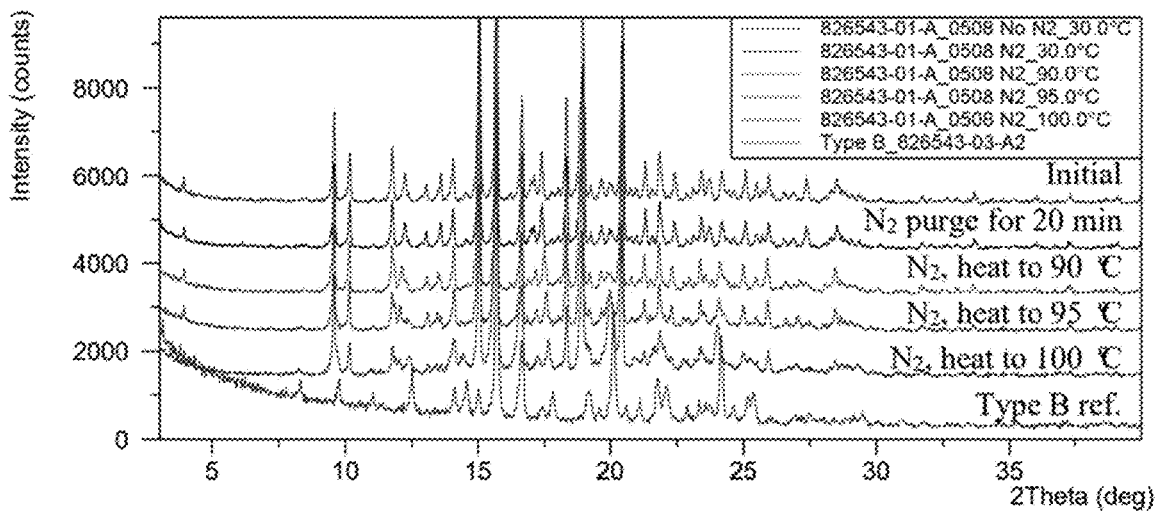
FIGS. 9 to 12 illustrate VT-XRPD patterns overlay of ABT-301 Type A.
Figure 10:
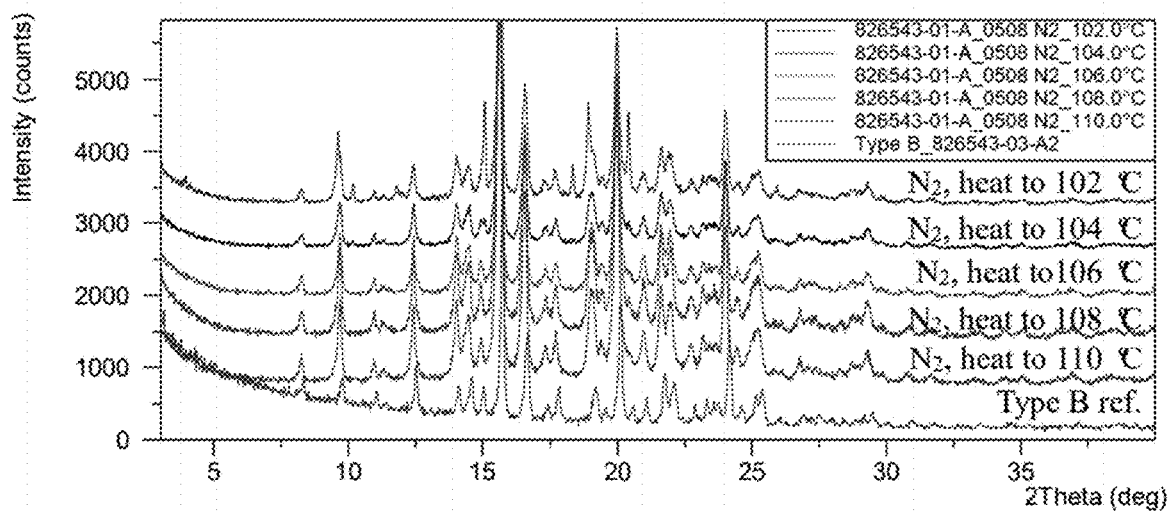
Figure 11:
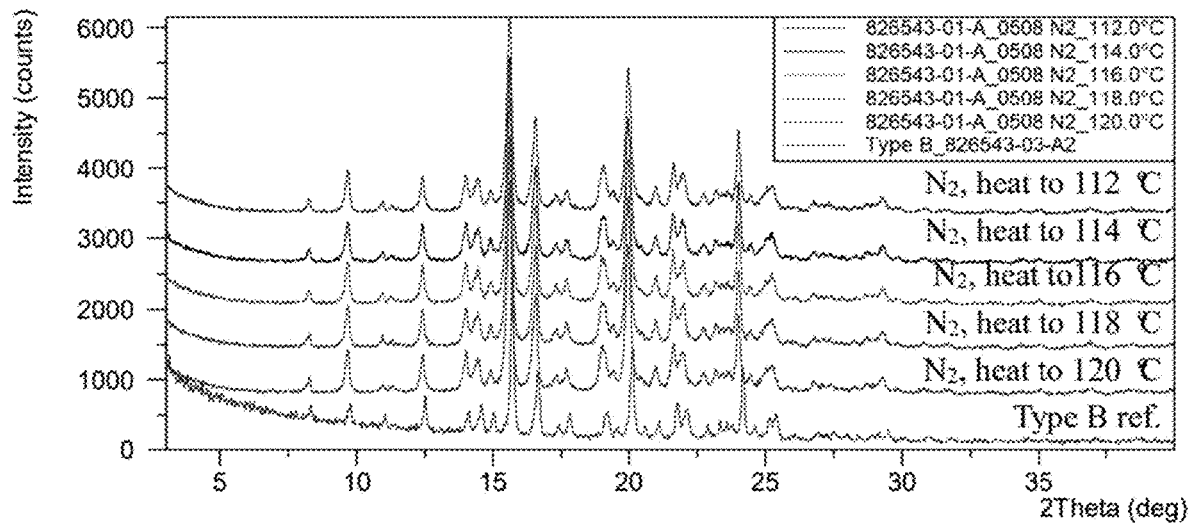
Figure 12:
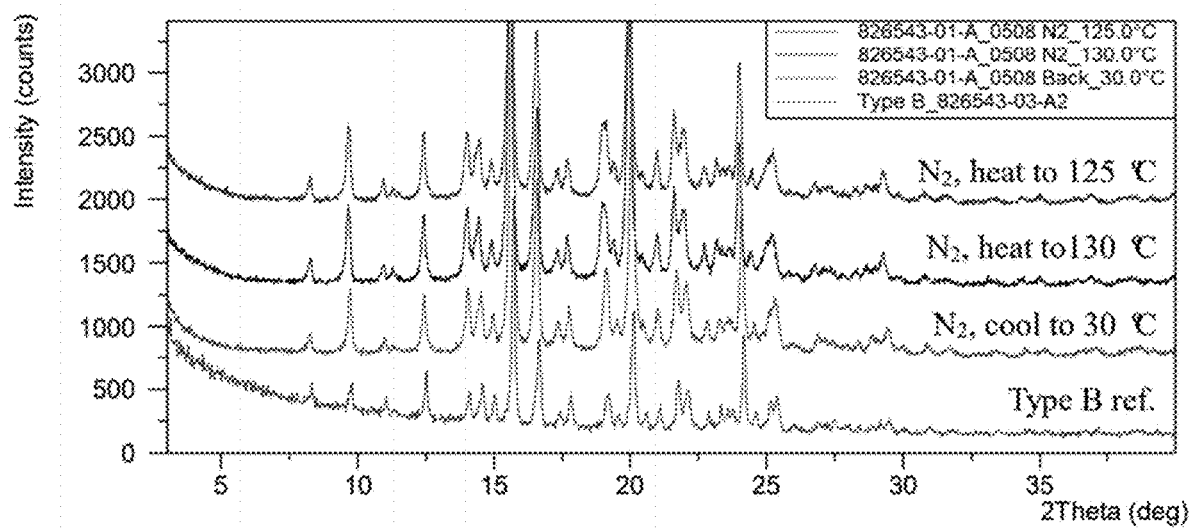

In order to investigate the TGA weight loss and DSC signals, heating experiment was performed for Type A. The results were displayed in FIG. 7. XRPD results showed that no form change was observed after heated to 100° C. and cooled to RT, which converted to a new form, named as Type B, after heated to 122° C./130° C. and cooled to RT. Melting with changed color was observed after heated to 180° C. and cooled to RT, and thus no XRPD test was performed. After heated to 100° C., TGA result (FIG. 8) showed a weight loss of 2.87% at up to 150° C., which showed no significant change for Type A before and after heating.

II. The Characterization Results of Type A

Figure 4:
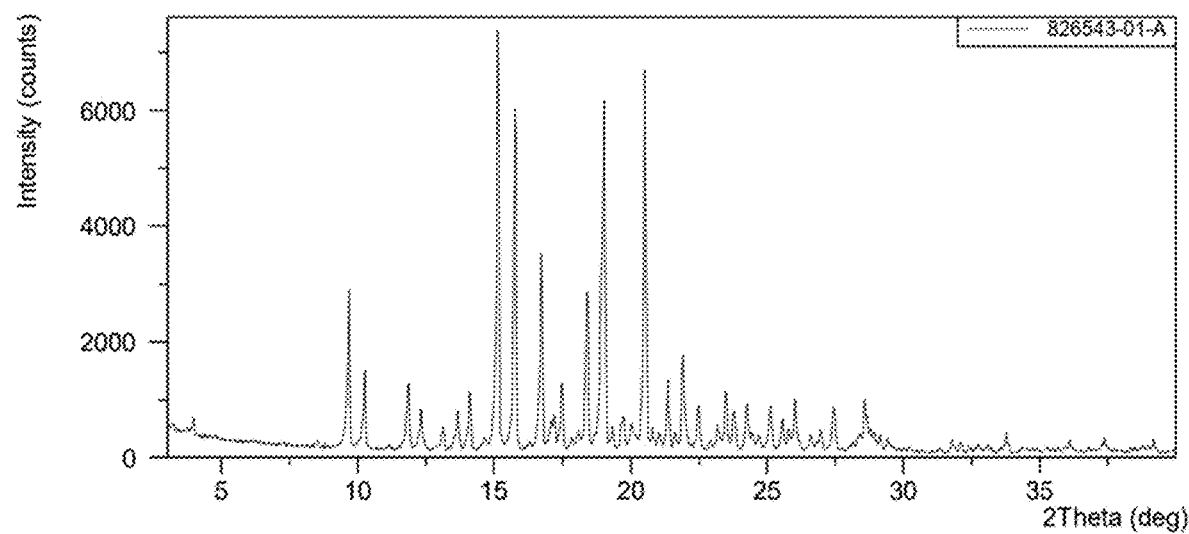
FIG. 4 illustrates a XRPD pattern for a crystalline form of ABT-301 Type A free base.
Figure 5:
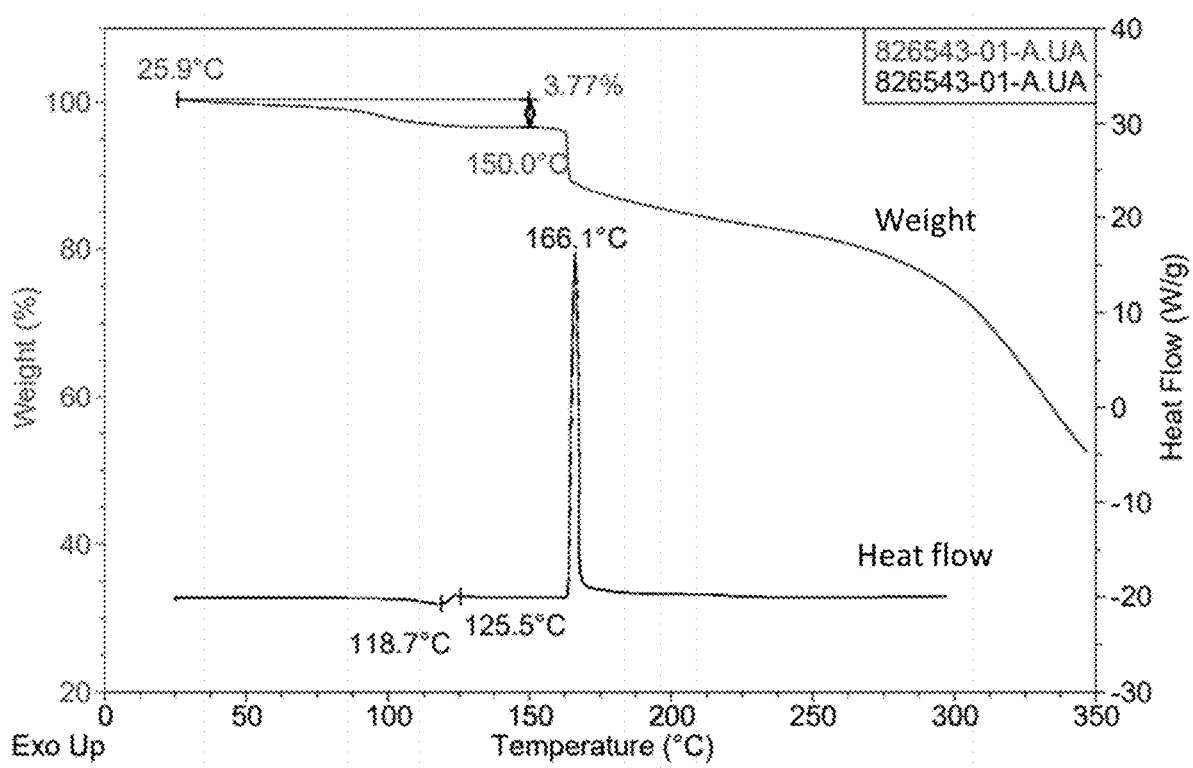
FIG. 5 illustrates TGA/DSC curves of ABT-301 Type A.
Figure 6:
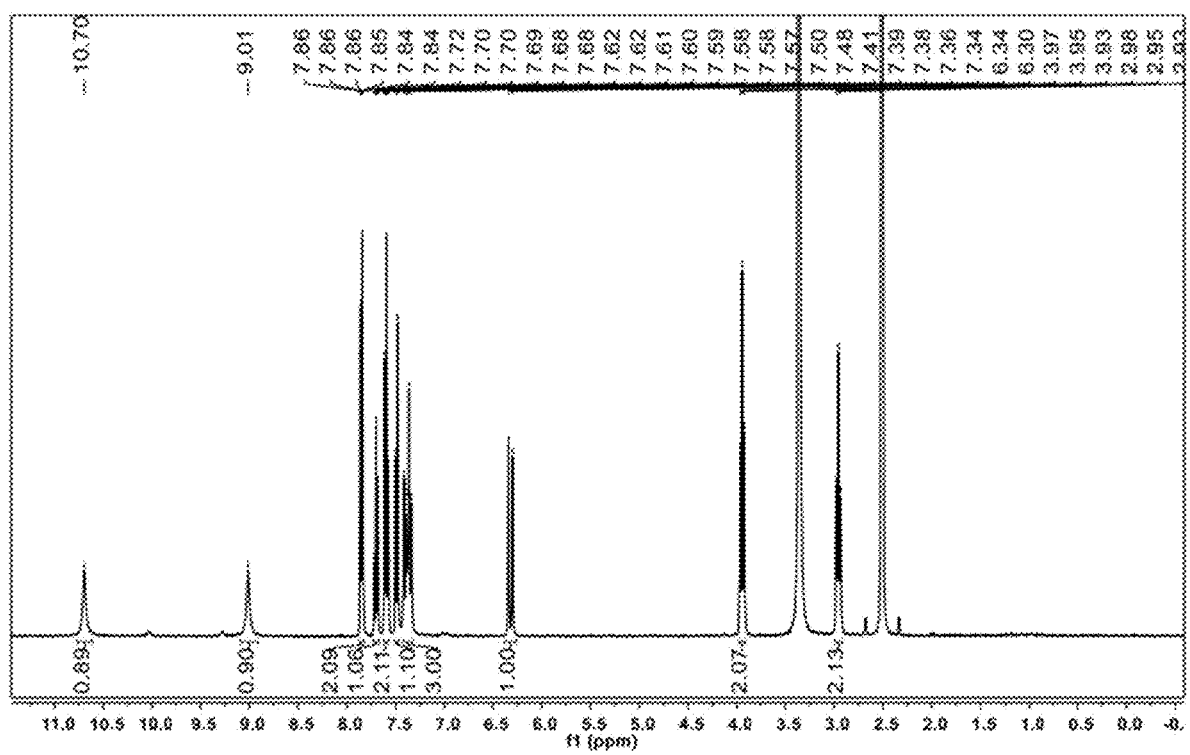
FIG. 6 illustrates 1H NMR spectrum of ABT-301 Type A.

XRPD pattern in FIG. 4 showed the starting material as received was crystalline. This material was named as Type A. The TGA/DSC curves of starting material were displayed in FIG. 5, which showed a weight loss of 3.77% at up to 150° C. and two endotherms at 118.7° C. and 125.5° C. (peak) with one exotherm at 166.1° C. (peak). The $^1$H NMR result was listed in FIG. 6. Approximate solubility of starting material was determined in 20 solvents at RT. Approximately 2 mg of sample was added into a 3-mL glass vial. Solvents in Table 2 were then added stepwise into the vials until the solids were dissolved visually or a total volume of 2 mL was reached. Solubility results summarized in Table 2 were used to guide the solvent selection in screening experiment design.

Figure 13:
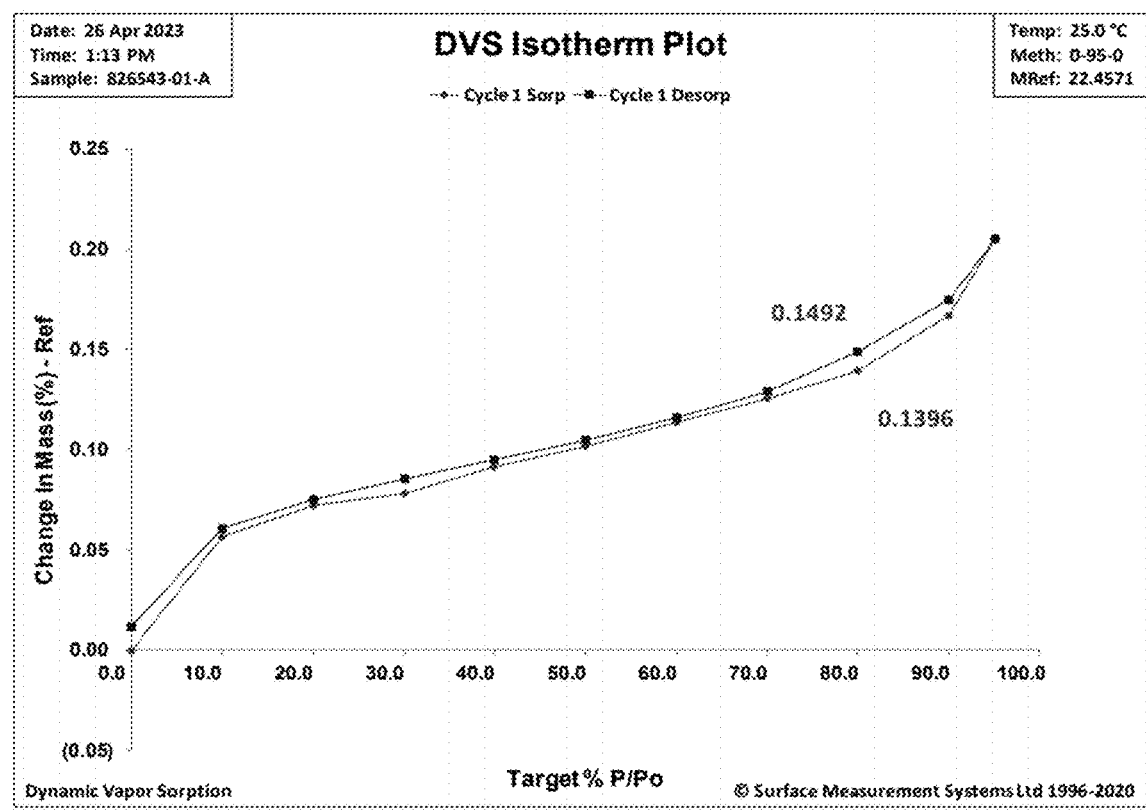
FIG. 13 illustrates DVS plot of ABT-301 Type A.
Figure 14:
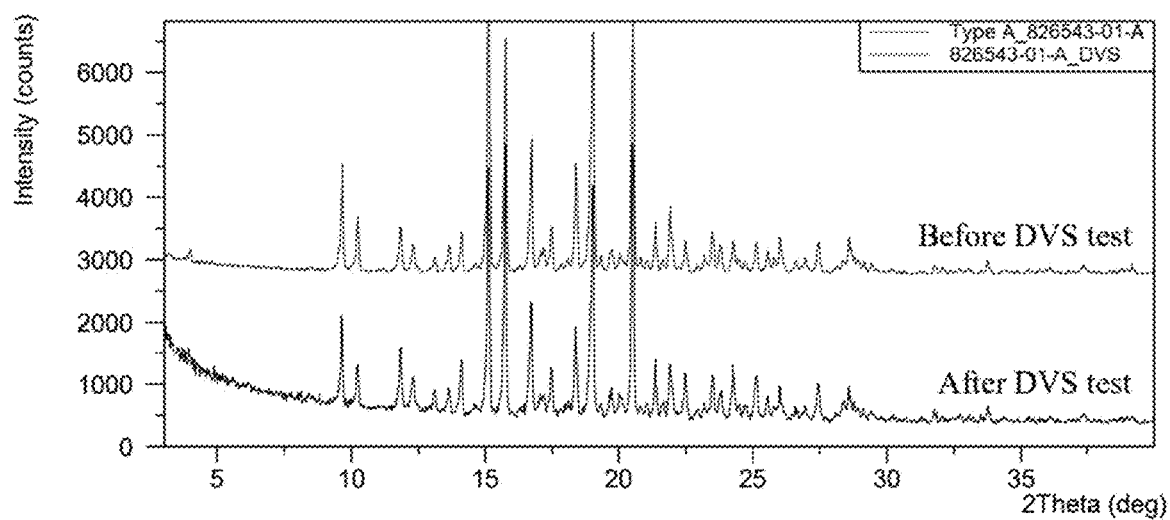
FIG. 14 illustrates XRPD pattern overlay of ABT-301 Type A before and after DVS.

Variable temperature XRPD (VT-XRPD) results (from FIG. 9 to FIG. 12) showed that no form change for Type A was observed after N2 purge for 20 min, and an extra peak was obtained after heated to 90, 95 and 100° C. under N2 purge, which almost converted to Type B after heated to 102 and 104° C. under N2 purge. The sample converted to Type B after heated to 106, 108, 110, 112, 114, 116, 118, 120, 125 and 130° C. under N2 purge (The peak shift at high temperature was postulated to be due to the thermal expansion of crystal lattice with the increased temperature), and no form change was observed for Type B after cooled to 30° C. under N2 purge. Combined with the TGA weight loss and form change during heating, Type A was postulated to be a hydrate. DVS result (FIG. 13) showed a water uptake of 0.1396% was observed at 25° C./80% RH. XRPD result (FIG. 14) showed that no form change was observed after DVS test.

III. The Characterization Results of Type B

Figure 15:
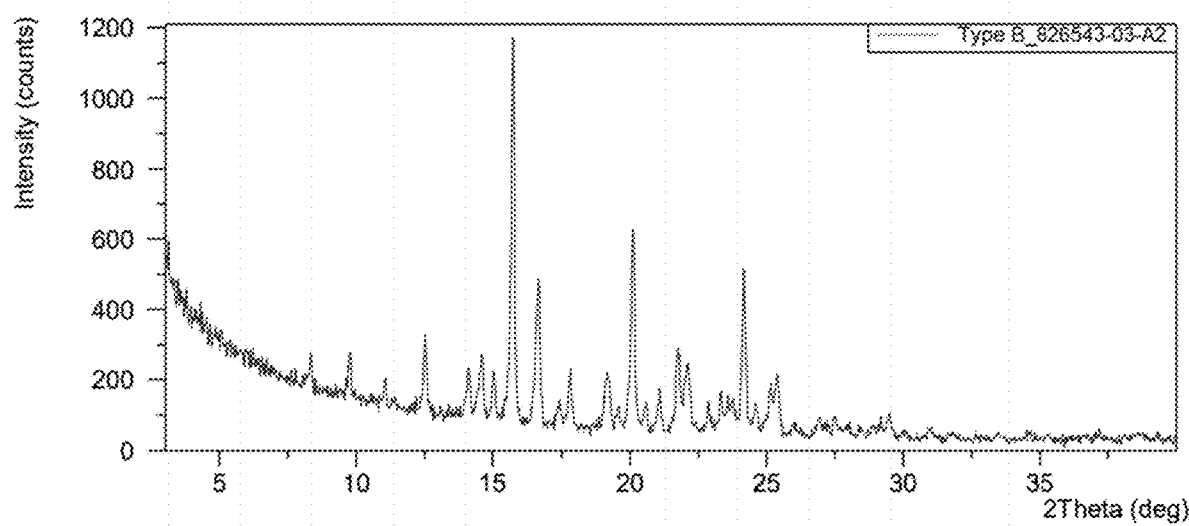
FIG. 15 illustrates a XRPD pattern for a crystalline form of ABT-301 Type B free base.
Figure 16:
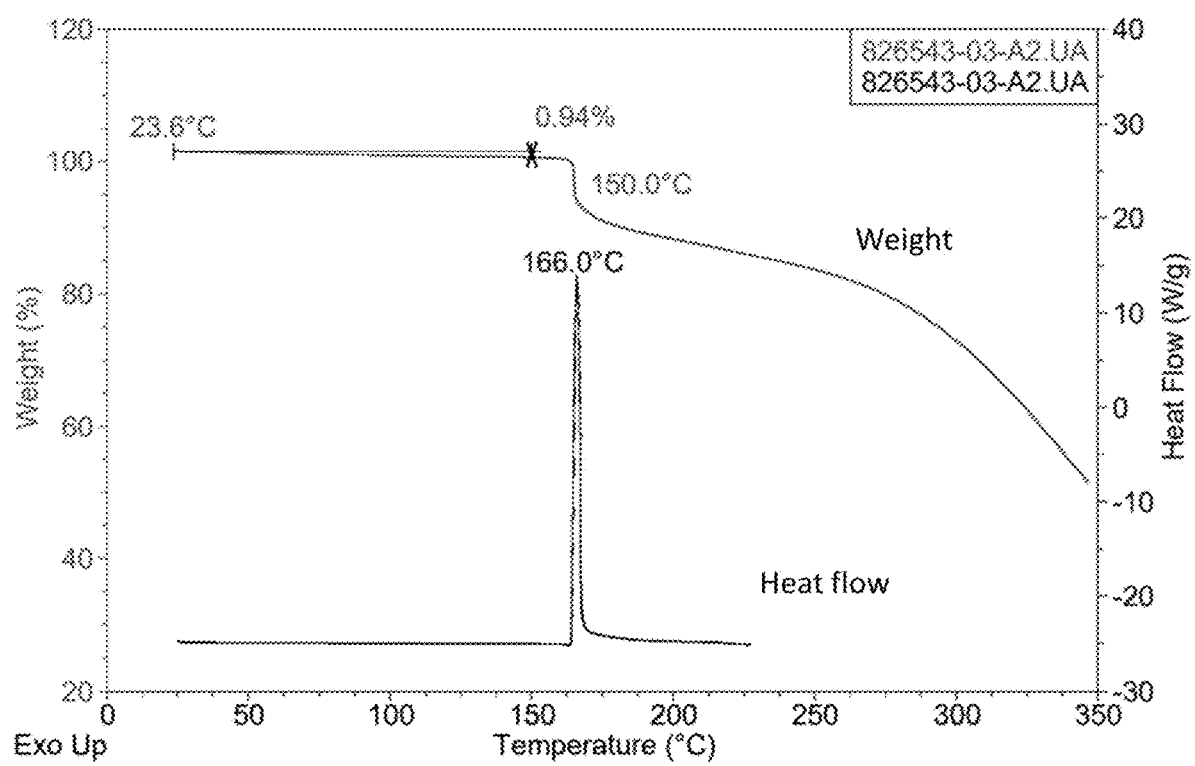
FIG. 16 illustrates TGA/DSC curves of ABT-301 Type B.
Figure 17:
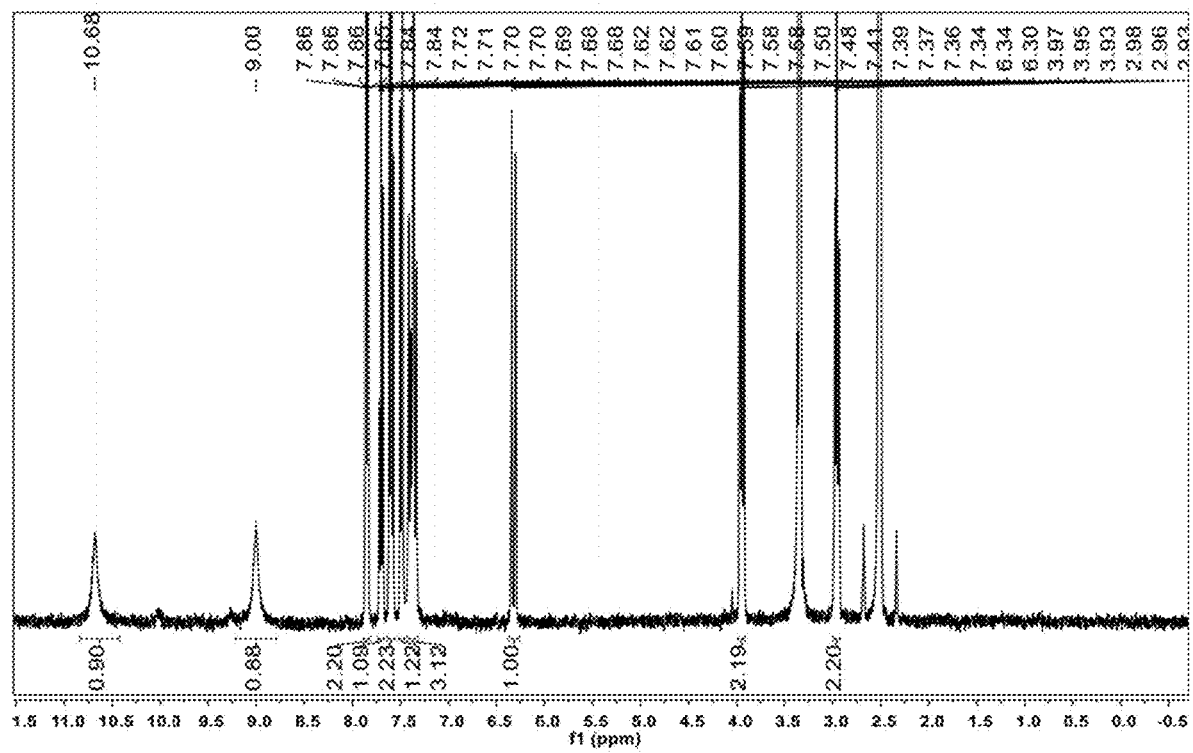
FIG. 17 illustrates 1H NMR spectrum of ABT-301 Type B.

Type B (826543-03-A2) was obtained by heating Type A to 122° C. followed by cooling to RT. The XRPD pattern was displayed in FIG. 15. The TGA/DSC results were displayed in FIG. 16, which showed a weight loss of 0.94% at up to 150° C. and one exotherm at 166.0° C. (peak). $^1$H NMR result was listed in FIG. 17. Due to the small TGA weight loss, Type B was postulated to be an anhydrate.

Figure 18:
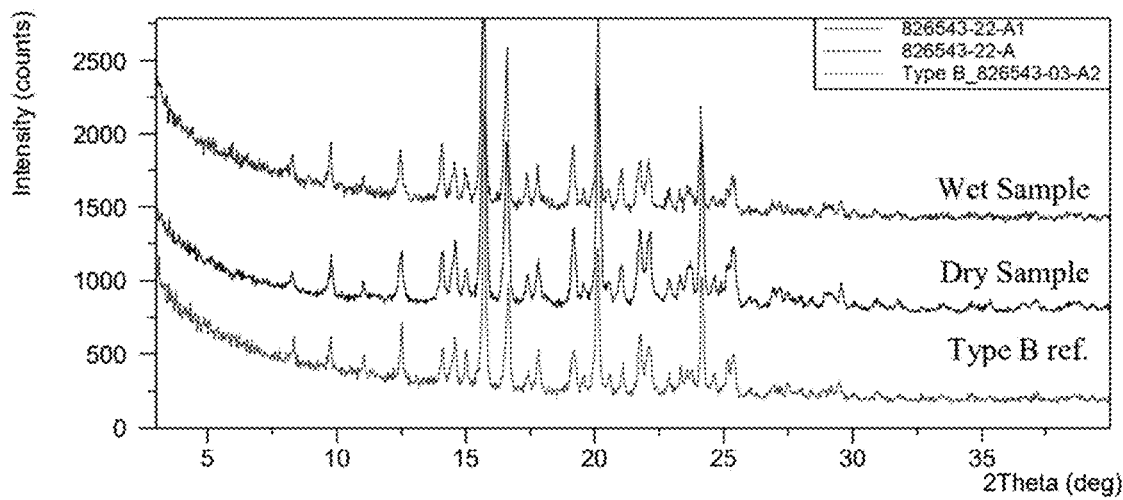
FIG. 18 illustrates a XRPD pattern overlay of re-preparation for ABT-301 Type B.
Figure 19:
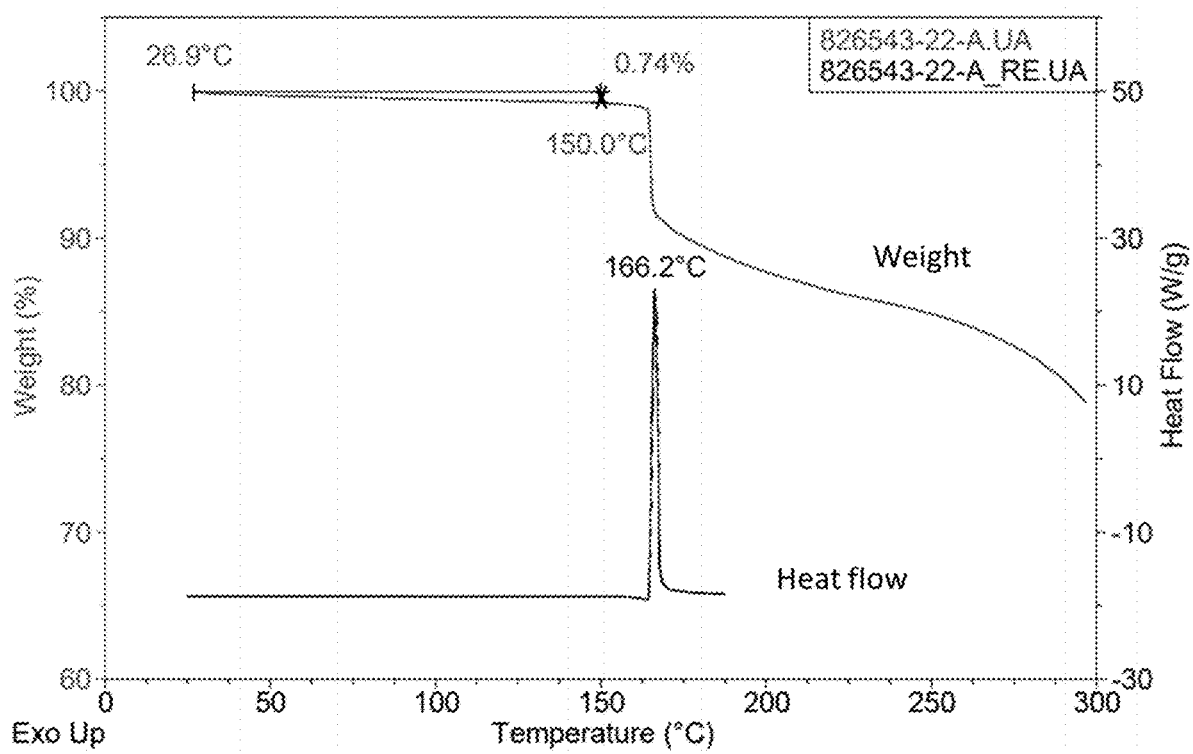
FIG. 19 illustrates TGA/DSC curves of ABT-301 Type B.
Figure 20:
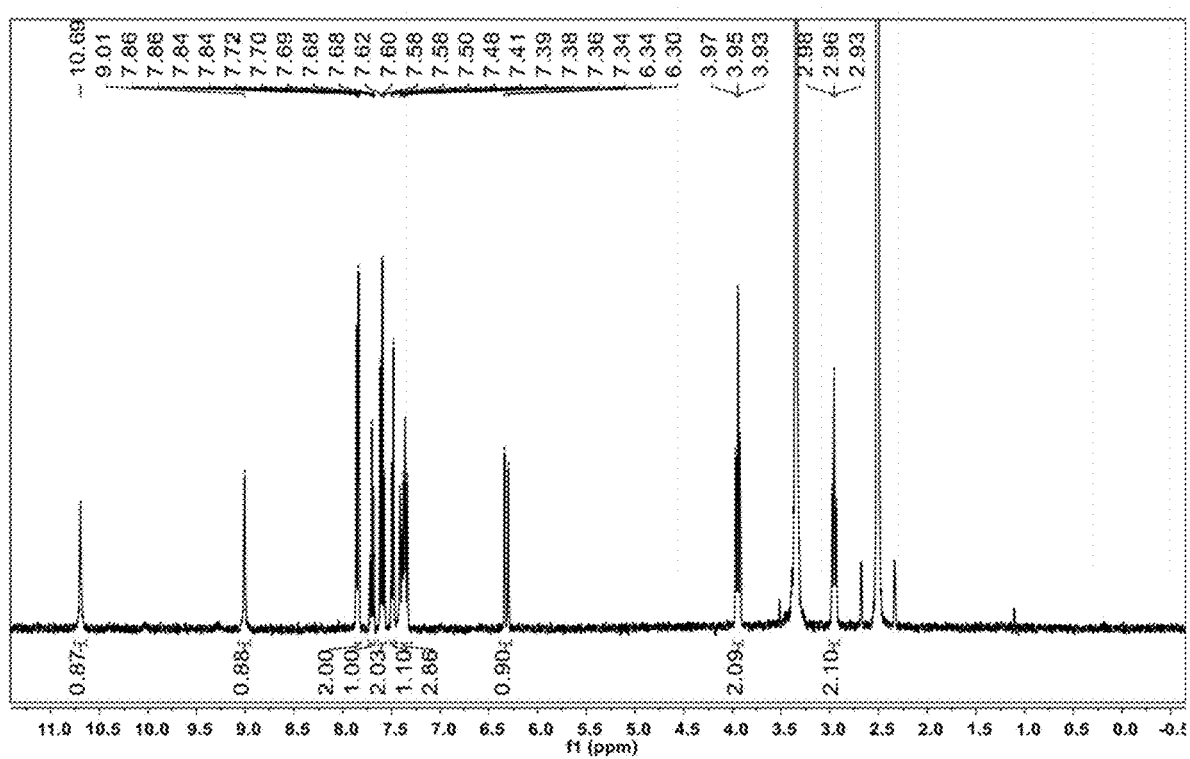
FIG. 20 illustrates 1H NMR spectrum of ABT-301 Type B.
Figure 21:
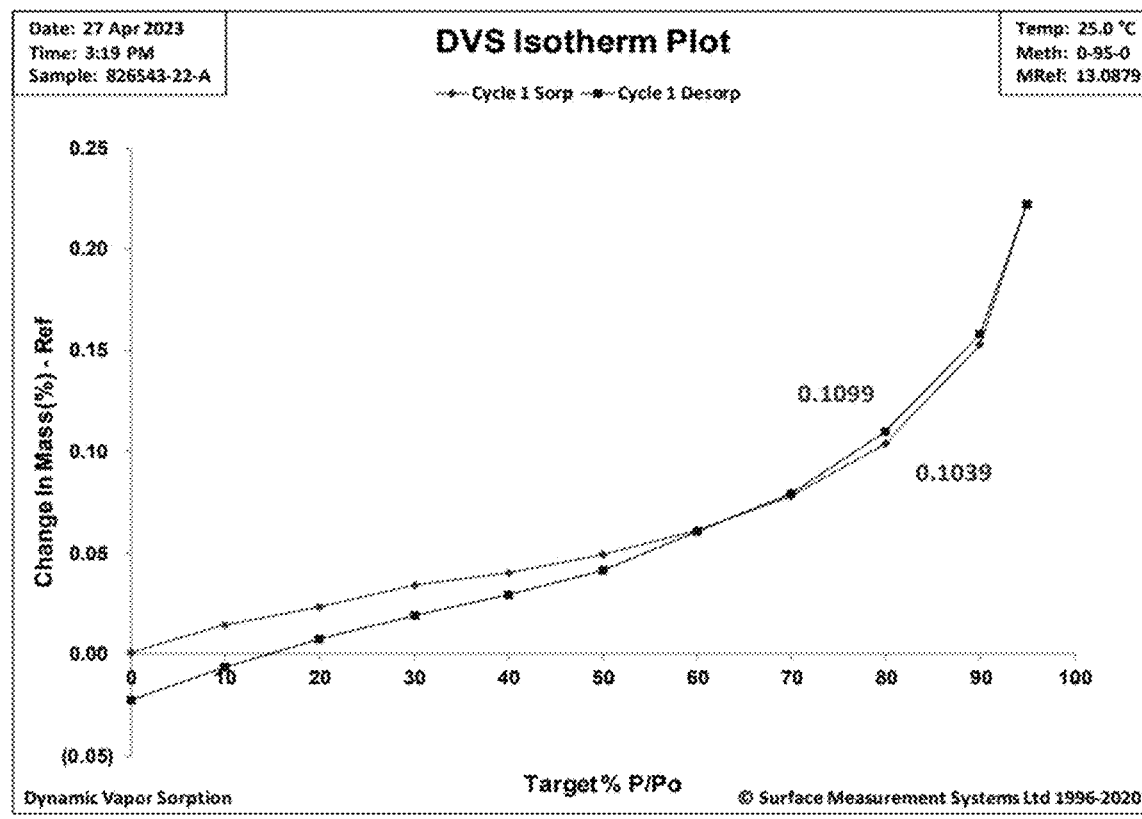
FIG. 21 illustrates DVS plot of ABT-301 Type B.
Figure 22:
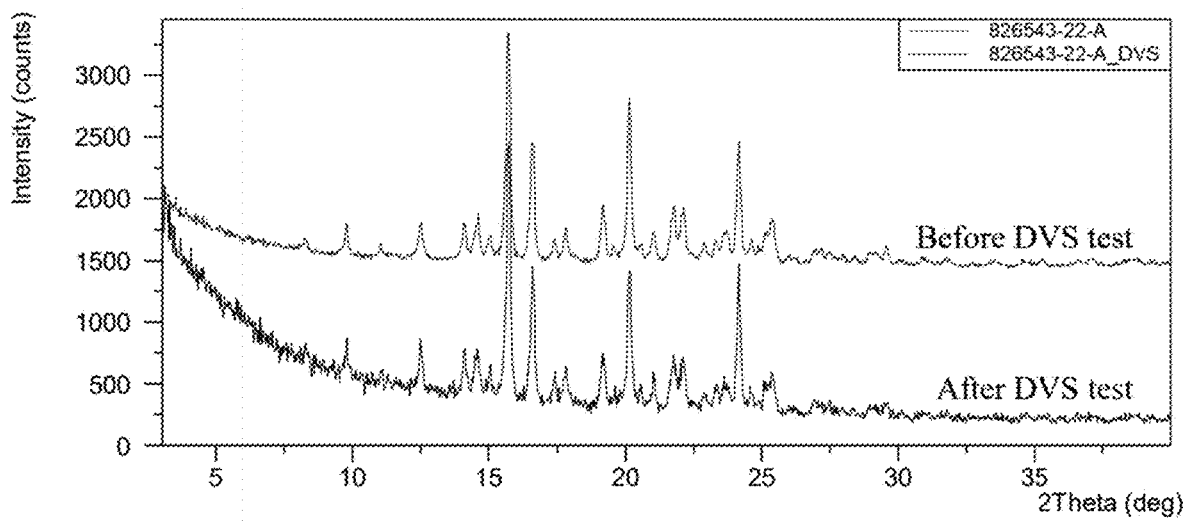
FIG. 22 illustrates XRPD pattern overlay of ABT-301 Type B before and after DVS.

Type B was attempted to be re-prepared on ~300 mg scale via slurry for further study. Type B (826543-22-A) was obtained by slurry of ~345 mg Type A in MTBE at 50° C. for 2 days followed by vacuum drying at RT for 1 day. (325 mg Type B was obtained and the yield was 94%) The XRPD pattern of Type B (826543-22-A) was shown in FIG. 18. The TGA/DSC curves were displayed in FIG. 19, which showed a weight loss of 0.74% at up to 150° C. and one exotherm at 166.2° C. (peak). The $^1$H NMR result in FIG. 20 showed no residual MTBE was detected. DVS result (FIG. 21) showed a water uptake of 0.1039% was observed at 25° C./80% RH. XRPD result (FIG. 22) showed that no form change was observed after DVS test.

IV. Inter-Conversion Relationship Study

Figure 23:
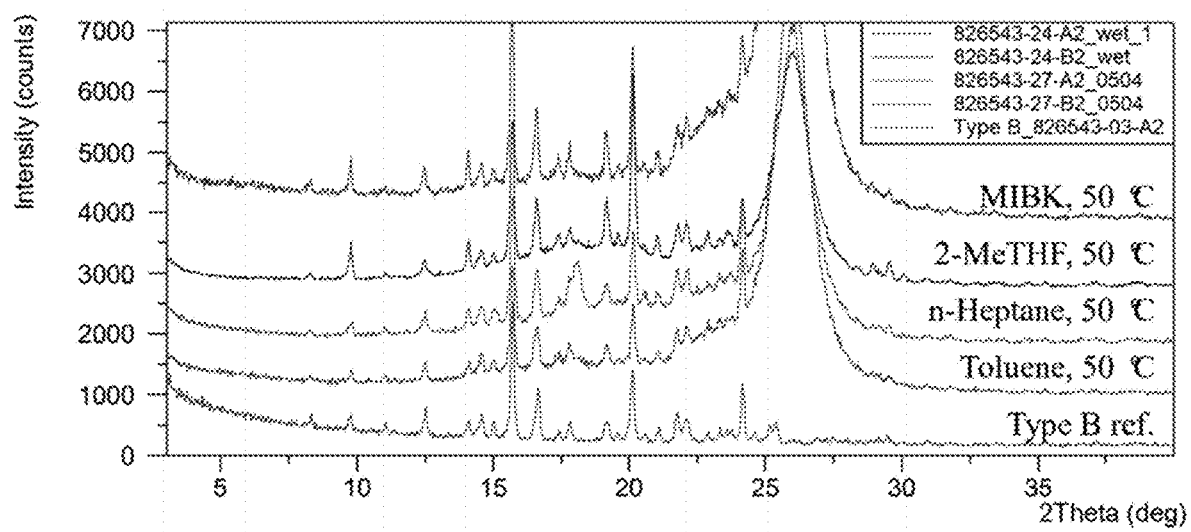
FIG. 23 illustrates XRPD pattern overlay of competitive slurry samples at 50° C.
Figure 24:
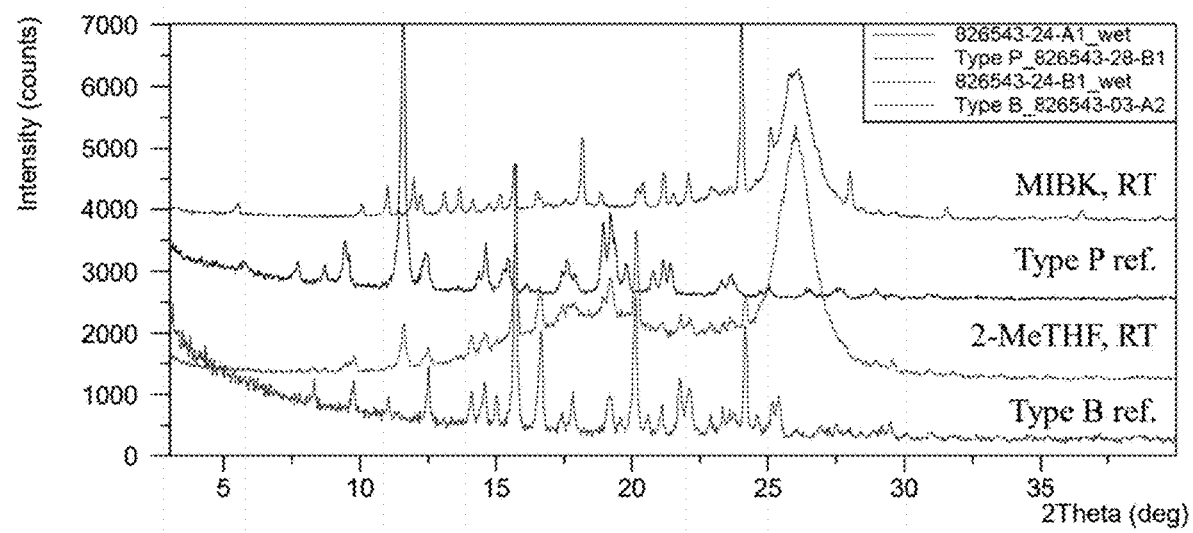
FIGS. 24 and 25 illustrate XRPD patterns overlay of competitive slurry samples at RT.
Figure 25:
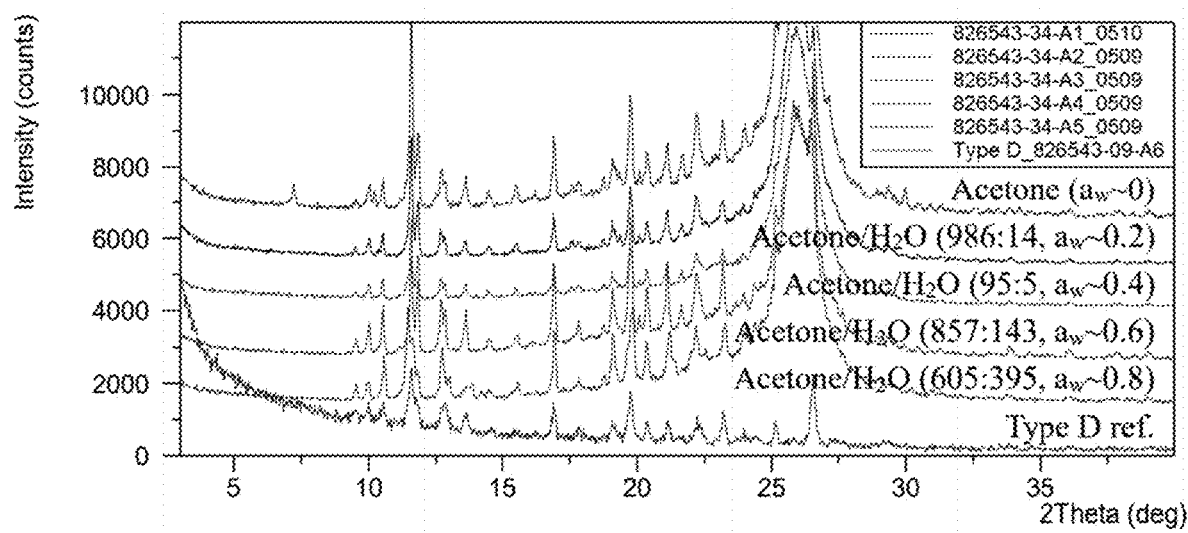

In order to investigate the inter-conversion relationship, competitive slurry experiments were performed for Type A and Type B in MIBK, 2-MeTHF, n-Heptane and Toluene at RT or 50° C. and in Acetone and Acetone/H$_2$O system with different water activities at RT. Around 10~20 mg Type A was weighed into 1.0 mL solvent for slurry at RT/50° C. The suspension samples were filtered, and the filtrate were transferred into each HPLC vial containing ~10 mg of Type A/B. Then the samples were stirred at RT/50° C. The results were summarized in Table 3, and the XRPD results were displayed from FIG. 23 to FIG. 25. The results showing Type B was obtained in MIBK, 2-MeTHF, n-Heptane and Toluene at 50° C. Solvate Type O was obtained in MIBK at RT, and a mixture of Type B and a meta-stable form Type P was obtained in 2-MeTHF at RT. Another solvate Type D was obtained in Acetone and Acetone/H$_2$O system with different water activities (aw 0.2~0.8) at RT.

TABLE 3

| Starting material | Expt. ID | Solvent (v/v) | Temp. | Time | Result |
|---|---|---|---|---|---|
| Type A | 826543-24-A1 | MIBK | RT | 2 days | Type O |
| (826543-01-A)/ | 826543-24-A2 | MIBK | 50° C. | 2 days | Type B |
| Type B | 826543-24-B1 | 2-MeTHF | RT | 2 days | Type B + P |
| (826543-22-A) | 826543-24-B2 | 2-MeTHF | 50° C. | 2 days | Type B |
| | 826543-27-A2 | n-Heptane | 50° C. | 8 days | Type B |
| | 826543-27-B2 | Toluene | 50° C. | 8 days | Type B |
| | 826543-34-A1 | Acetone (a$_w$~0) | RT | 2 days | Type D |
| | 826543-34-A2 | Acetone/H$_2$O (986:14, a$_w$~0.2) | RT | 1 day | Type D |
| | 826543-34-A3 | Acetone/H$_2$O (95:5, a$_w$~0.4) | RT | 1 day | Type D |
| | 826543-34-A4 | Acetone/H$_2$O (857:143, a$_w$~0.6) | RT | 1 day | Type D |
| | 826543-34-A5 | Acetone/H$_2$O (605:395, a$_w$~0.8) | RT | 1 day | Type D |

Figure 26:
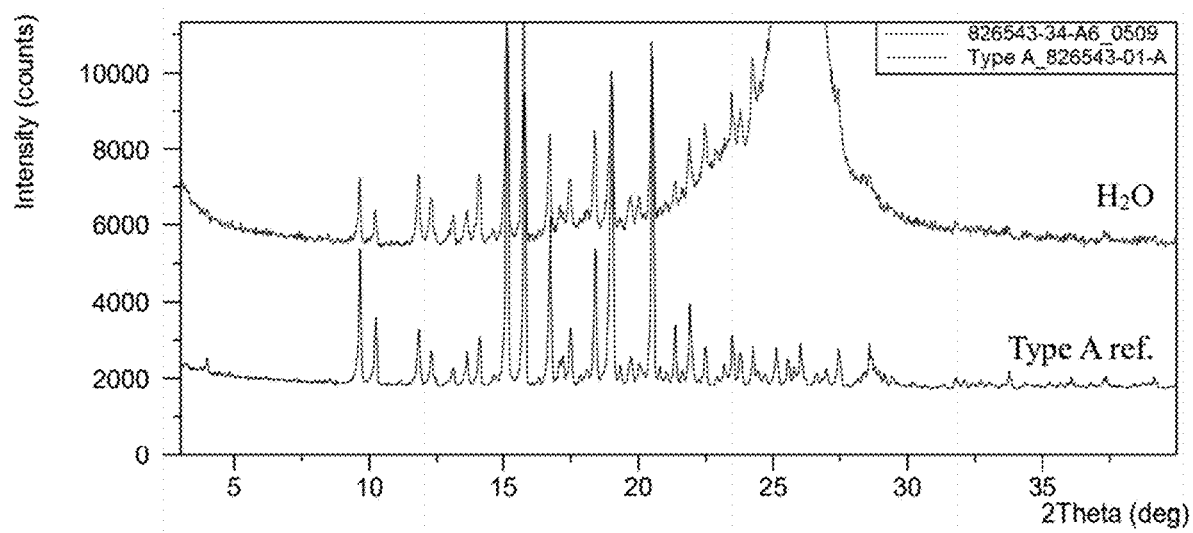
FIG. 26 illustrates XRPD pattern overlay of competitive slurry samples in $H_2O$ at RT.
Figure 27:
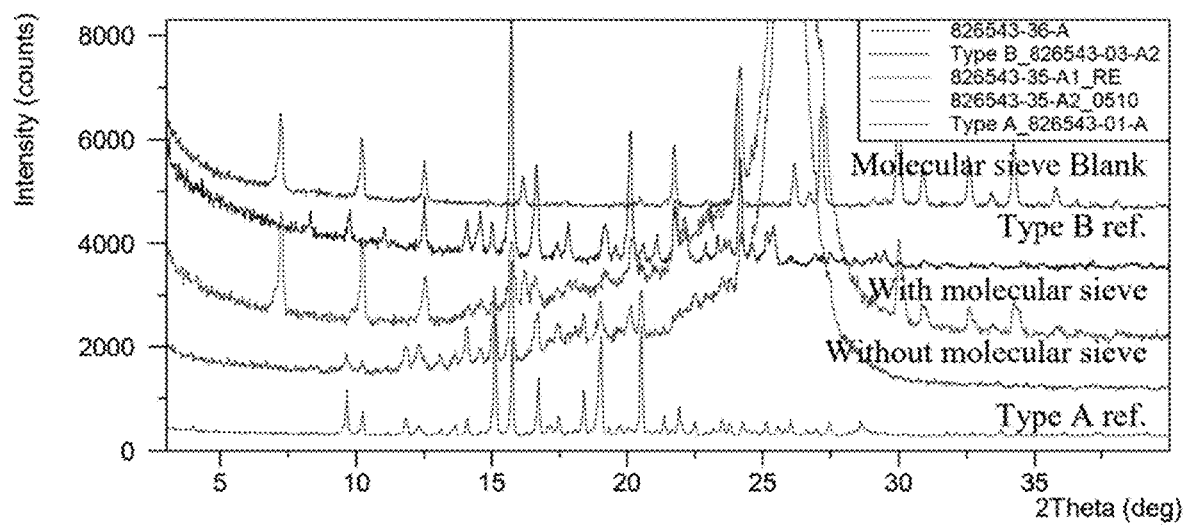
FIG. 27 illustrates XRPD pattern overlay of competitive slurry samples in n-Heptane at RT.
Figure 28:
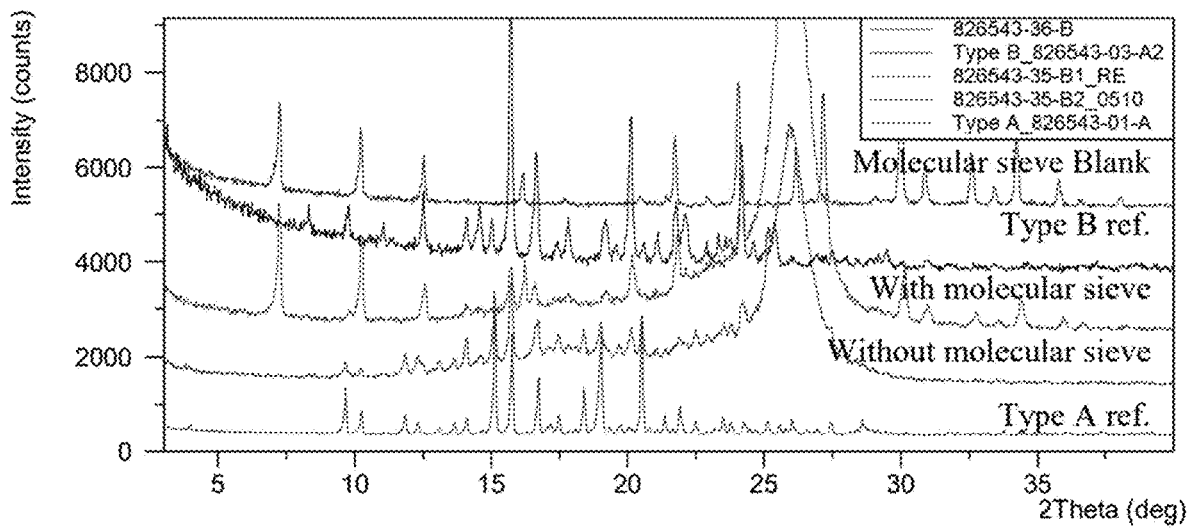
FIG. 28 illustrates XRPD pattern overlay of competitive slurry samples in Toluene at RT.

Based on the results of competitive slurry, additional competitive slurry experiments were performed. Around 10 mg Type A was weighed into each solvent followed by slurry at RT with molecular sieve. The suspension samples were filtered, and the filtrate were transferred into each HPLC vial containing ~10 mg of Type A and Type B. Then the samples were stirred at RT with or without molecular sieve. After the competitive slurry, the suspension samples were filtered, and KF test was performed for the filtrate. The results were summarized in Table 4, and the XRPD results were displayed from FIG. 26 to FIG. 28. The results showed Type A was obtained at RT in H$_2$O. Type B was obtained in n-Heptane and Toluene at RT with molecular sieve for 2 days, and Type A was obtained in n-Heptane and Toluene at RT without molecular sieve for 1 day. KF test was performed for the filtrates after competitive slurry, and the results showed lower water content with molecular sieve, in which Type B was obtained. The results showed the inter-conversion relationship between Type A and Type B was related to the water content.

TABLE 4

| Starting material | Expt. ID (826543-) | Solvent | Temp. | Time | Result | KF (water content) | Water activity** |
|---|---|---|---|---|---|---|---|
| Type A | 34-A6 | H$_2$O | RT | 1 day | Type A | — | — |
| (826543-01-A)/ | 35-A1* | n-Heptane | RT | 2 days | Type B | 0.0003 wt % | 0.02 |
| Type B | 35-A2# | n-Heptane | RT | 1 day | Type A | 0.0049 wt % | 0.29 |
| (826543-22-A) | 35-B1* | Toluene | RT | 2 days | Type B | 0.0072 wt % | 0.11 |
| | 35-B2# | Toluene | RT | 1 day | Type A | 0.0250 wt % | 0.32 |

*Slurry with molecular sieve.
Slurry without molecular sieve.
**The water activity was calculated by software COSMOlogic based on KF results. Since water is immiscible with n-Heptane and Toluene, the water activity results were just for reference.

Figure 29:
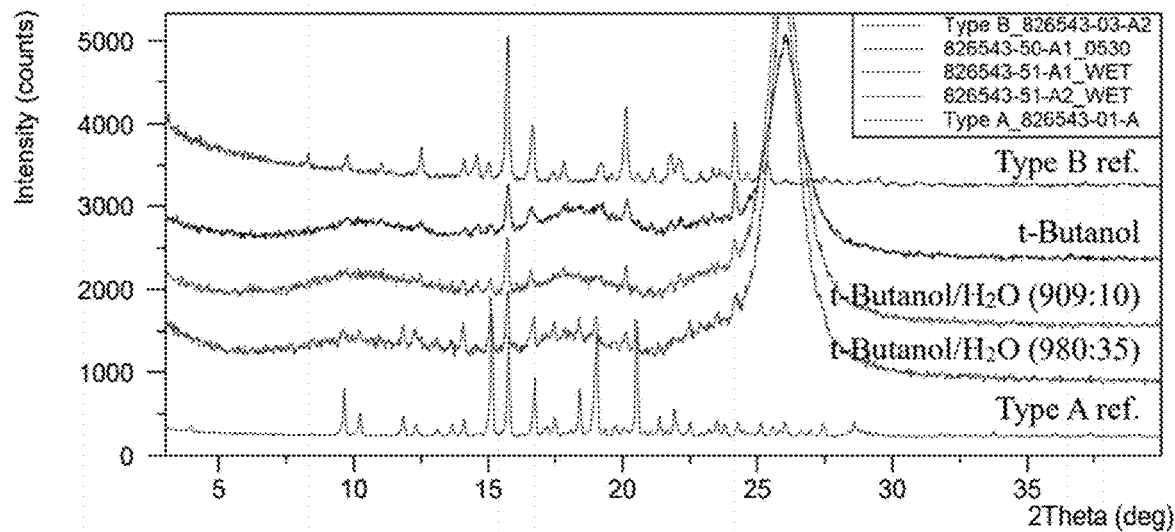
FIGS. 29 and 30 illustrate XRPD pattern overlay of competitive slurry samples at RT with different water activities.
Figure 30:
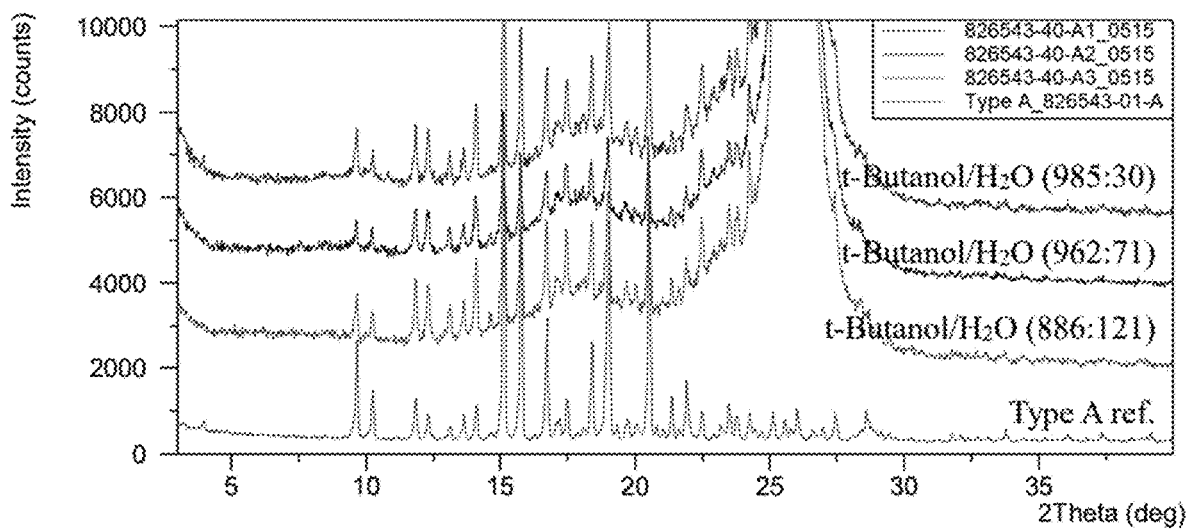

Another solvent system t-Butanol/H$_2$O was used for additional competitive slurry experiments. Around 10 mg Type A was weighed into 1.0 mL solvent for slurry in t-Butanol and t-Butanol/H$_2$O with different water contents at RT. The suspension samples were filtered, and the filtrate were transferred into each HPLC vial containing ~10 mg of Type A/B. Then the samples were stirred at RT. After the competitive slurry, the suspension samples were filtered, and KF test was performed for the filtrate. Water activity was calculated based on the KF results using software COSMOlogic. The results were summarized in Table 5, and the XRPD results were displayed in FIG. 29 and FIG. 30. The results showed that Type B was obtained with water activity ≤0.17, and Type A was obtained with water activity ≥0.37 at RT.

TABLE 5

| Starting material | Expt. ID (826543-) | Solvent (v/v) | Temp. | Time | Result | KF (water content) | Water activity* |
|---|---|---|---|---|---|---|---|
| Type A (826543-01-A)/ Type B (826543-22-A) | 50-A1 | t-Butanol# | RT | 1 day | Type B | 0.6066% | 0.06 |
| | 51-A1 | t-Butanol/H$_2$O (909:10)# | RT | 1 day | Type B | 1.8264% | 0.17 |
| | 51-A2 | t-Butanol/H$_2$O (980:35)# | RT | 1 day | Type A | 4.6553% | 0.37 |
| | 40-A1 | t-Butanol/H$_2$O (985:30) | RT | 3 days | Type A | 8.1820% | 0.56 |
| | 40-A2 | t-Butanol/H$_2$O (962:71) | RT | 3 days | Type A | 11.7785% | 0.71 |
| | 40-A3 | t-Butanol/H$_2$O (886:121) | RT | 3 days | Type A | 18.4285% | 0.88 |

*The water activity was calculated by software COSMOlogic based on KF results.
In order to obtain low water activity, t-Butanol was used from a new bottle with lower water content.

Based on the above results, the inter-conversion relationship between Type A and Type B were related to the water content (or water activity) and temperature. Therefore, it was suggested to perform further evaluation (e.g. solid stability) for both forms, and then select a lead form for further development. Additionally, since many solvates were observed for this compound, it was suggested to pay attention to the solvent selection during further crystallization process study.

Methods

Solvents Used

The solvent abbreviations are listed in Table 6.

TABLE 6

| Abbreviation | Solvent | Abbreviation | Solvent |
|---|---|---|---|
| MeOH | Methanol | THF | Tetrahydrofuran |
| EtOH | Ethanol | 2-MeTHF | 2-Methyltetrahydrofuran |

TABLE 6-continued

| Abbreviation | Solvent | Abbreviation | Solvent |
|---|---|---|---|
| IPA | Isopropyl alcohol | DCM | Dichloromethane |
| MIBK | 4-Methyl-2-pentanone | ACN | Acetonitrile |
| EtOAc | Ethyl acetate | DMSO | Dimethylsulfoxide |
| IPAc | Isopropyl acetate | DMAc | N,N-Dimethylacetamide |
| MTBE | Methyl tert-butyl ether | NMP | 1-Methyl-2-pyrrolidone |

Polymorph Screening

A total of 100 polymorph screening experiments were performed using different crystallization or solid transformation methods. The methods utilized and results were summarized in Table 7.

TABLE 7

| Method | No. of Experiment | Result |
|---|---|---|
| Vapor-solution diffusion | 14 | Type A/D/F/G/H/M/Amorphous |
| Vapor-solid diffusion | 12 | Type A/C/D/K/L/M/E + B |
| Slow evaporation | 6 | Type D/E/F/H/K/N |
| Slurry at RT | 17 | Type A/B/C/E/F/I/J/L/M |
| Slurry at 50° C. | 12 | Type A/B/C/E/F/G/K |
| Temperature cycling | 11 | Type A/B/C/D/E/F/G/I/J/K/A + B |

TABLE 7-continued

| Method | No. of Experiment | Result |
|---|---|---|
| Slow cooling | 6 | Type A/C/E/I/K/A + B |
| Anti-solvent addition | 20 | Type A/B/E/F/J/A + B/A + D/A + F/Amorphous |
| Grinding | 2 | Amorphous |
| Total | 100 | Type A/B/C/D/E/F/G/H/I/J/K/L/M/N/A + B/A + D/A + F/E + B/Amorphous |

Vapor-Solution Diffusion

Vapor-solution diffusion experiments were conducted under 14 different conditions. Approximately 20 mg of starting material (826543-01-A) was dissolved in 0.5~1.0 mL of appropriate solvent to obtain a clear solution in a 3-mL vial, and filtered to a new vial (0.45 μm, PTFE). This solution was then placed into a 20-mL vial with 3 mL of volatile solvent. The 20-mL vial was sealed with a cap and kept at RT allowing sufficient time for organic vapor to interact with the solution. The solids were isolated for XRPD analysis.

Vapor-Solid Diffusion

Vapor-solid diffusion experiments were conducted using 12 different solvents. Approximately 20 mg of starting material (826543-01-A) was weighed into a 3-mL vial, which was placed into a 20-mL vial with 3 mL of volatile solvent. The 20-mL vial was sealed with a cap and kept at RT for 7 days allowing solvent vapor to interact with sample.

Slow Evaporation

Slow evaporation experiments were performed under 6 conditions. 20 mg of starting material (826543-01-A) was dissolved in 1.0~2.0 mL of solvent in a 3-mL glass vial. The resulting solution was subjected to slow evaporation at RT with vials sealed and poked with 4 pinholes.

Slurry at RT

About 20 mg of starting material (826543-05-A) was suspended in 0.5 mL of solvent in an HPLC glass vial. After the suspension was stirred magnetically (1000 rpm) at RT for 3 days, the remaining solids were centrifuged for XRPD analysis.

Slurry at 50° C.

About 20 mg of starting material (826543-01-A) was suspended in 0.5 mL of solvent in an HPLC glass vial. After the suspension was stirred (1000 rpm) at 50° C. for 4 days, the remaining solids were centrifuged for XRPD analysis.

Temperature Cycling

About 20 mg of starting material (826543-01-A) was suspended in 0.5 mL of solvent in an HPLC glass vial. After heating-cooling (50° C.~5° C., 0.1° C./min) was performed for the suspension for 2 cycles, the remaining solids were centrifuged for XRPD analysis.

Slow Cooling

Slow cooling experiments were conducted in 6 solvent systems. 20 mg of starting material (826543-01-A) was suspended in 1.0~2.0 mL of solvent in a 3-mL glass vial at RT. The suspension was then heated to 50° C., equilibrated for 2 hrs and filtered to a new vial (0.45 μm, PTFE). Filtrates were slowly cooled down to 5° C. at a rate of 0.1° C./min. The obtained solids were kept isothermal at 5° C. and then solids were tested by XRPD.

Anti-Solvent Addition

A total of 20 anti-solvent addition experiments were carried out. About 20 mg of starting material (826543-01-A) was dissolved in 0.6~1.2 mL solvent to obtain a clear solution, filtered the solution to a new vial (0.45 μm, PTFE) if the solids were not dissolved, and the solution was magnetically stirred (~1000 rpm) followed by addition of anti-solvent until precipitate appeared or the total amount of anti-solvent reached 10.0 mL. The samples without precipitate were transferred to slurry at 5° C. and then transferred to slurry at −20° C. The clear samples were transferred to RT for evaporation. The solids were isolated for XRPD analysis.

Grinding

Grinding experiments were performed with or without solvent addition. Approximate 20 mg of starting material (826543-01-A) was weighed into the mortar. 20 μL solvent was added into the mortar. The solids were grinded for 3~5 min. The solids were isolated for XRPD analysis.

XRPD

For XRPD analysis, PANalytical X-ray powder diffract meters were used. The XRPD parameters used are listed in Table 8.

TABLE 8

| Parameters | X' Pert3 or Empyrean | Empyrean (VT-XRPD) |
|---|---|---|
| X-Ray wavelength | Cu, Kα; Kα1 (Å): 1.540598 Kα2 (Å): 1.544426 intensity ratio Kα2/Kα1: 0.50 | Cu, Kα; Kα1 (Å): 1.540598 Kα2 (Å): 1.544426 intensity ratio Kα2/Kα1: 0.50 |
| X-Ray tube setting | 45 kV, 40 mA | 45 kV, 40 mA |
| Divergence slit | ⅛° | ⅛° |
| Scan mode | Continuous | Continuous |
| Scan range (2θ/°) | 3~40 | 3~40 |
| Step size (2θ/°) | 46.7 | 17.8 |
| Scan step time (s) | 0.0263 | 0.0167 |
| Test time | About 5 min | About 10 min |

TGA and DSC

TGA data were collected using TA Discovery 5500 TGA from TA Instruments. DSC was performed using TA Discovery 2500 DSC and TA Discovery DSC250 from TA Instruments. Detailed parameters used are listed in Table 9.

TABLE 9

| Parameters | TGA | DSC |
|---|---|---|
| Method | Ramp | Ramp |
| Sample pan | Aluminum, open | Aluminum, crimped/open |
| Temperature | RT-Target temperature | 25° C.-Target temperature |
| Heating rate | 10° C./min | 10° C./min |
| Purge gas | $N_2$ | $N_2$ |

Solution NMR

Solution NMR was collected on Bruker 400M NMR Spectrometer using DMSO-do and MeOD.

DVS

DVS was measured via a SMS (Surface Measurement Systems) DVS Intrinsic or Intrinsic Plus. The relative humidity at 25° C. were calibrated against deliquescence point of LiCl, $Mg(NO_3)_2$ and KCl. The DVS test parameters are listed in Table 10.

TABLE 10

| Parameters | Values |
| --- | --- |
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH-95% RH |
| RH step size | 10% (90% RH-0% RH-90% RH) |
| | 5% (95% RH-90% RH and 90% RH-95% RH) |

Karl Fishcher (KF)

The instrument (Metrohm 870 KF Titrinoplus) is calibrated using purified water and the titration reagent is Hydranal® R-Composite 5 provided by Sigma-aldrich. Methanol (HPLC grade) is used to dissolve samples.

Example 3

Single Crystal Structure Determination for ABT-301 Type A and B

In the Example 2, Type A and Type B were identified to be a hydrate and an anhydrate, respectively. For the further study, this single crystal study is to further investigate the single crystal structure of Type A and Type B through single crystal growth and single crystal X-ray diffraction (SCXRD) analysis.

I. Single Crystal Growth

Figure 31:
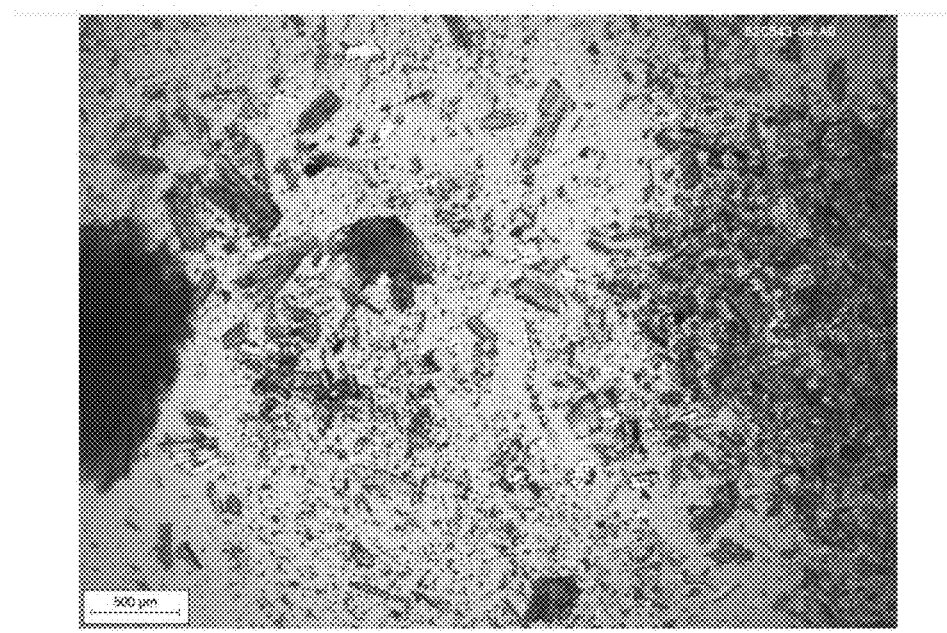
FIG. 31 illustrates PLM image of the ABT-301 Type A single crystal.
Figure 32:
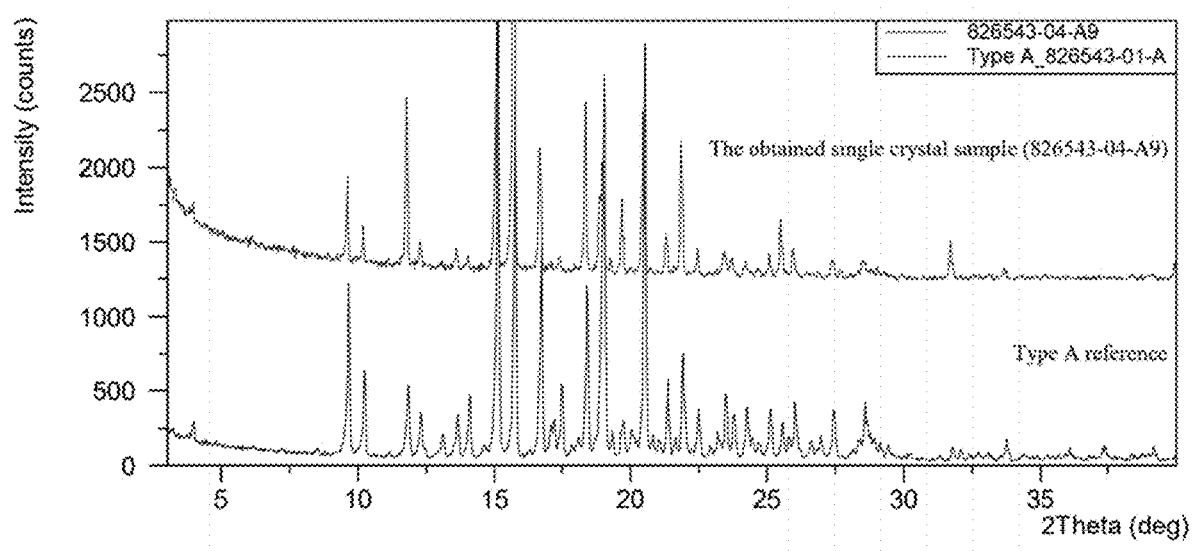
FIG. 32 illustrates XRPD pattern overlay of ABT-301 Type A single crystal and Type A reference.

The single crystal sample (CP ID: 826543-04-A9) of ABT-301 Type A was obtained from liquid-vapor diffusion experiment system (solvent: 1,4-Dioxane; anti-solvent: Toluene) in the previous polymorph screening study. The growth experiment details are elaborated below:

20.4 mg ABT-301 Type A starting material was weighed into a 3 mL glass vial with the addition of 1.0 mL 1,4-dioxane to make a sample solution. The glass vial was enclosed in a 20 mL glass vial prefilled with 3 mL toluene (as an anti-solvent) to perform liquid-vapor diffusion at room temperature. After 6 day's evaporation, plank-like single crystals was obtained, as shown in FIG. 31. The single crystal was then characterized by XRPD. XRPD patterns overlay (FIG. 32) indicated that the experimental XRPD of the obtained single crystal is consistent with that of the ABT-301 Type A reference (CP ID: 826543-01-A).

Figure 33:
FIG. 33 illustrates PLM image of the ABT-301 Type B single crystal.
Figure 34:
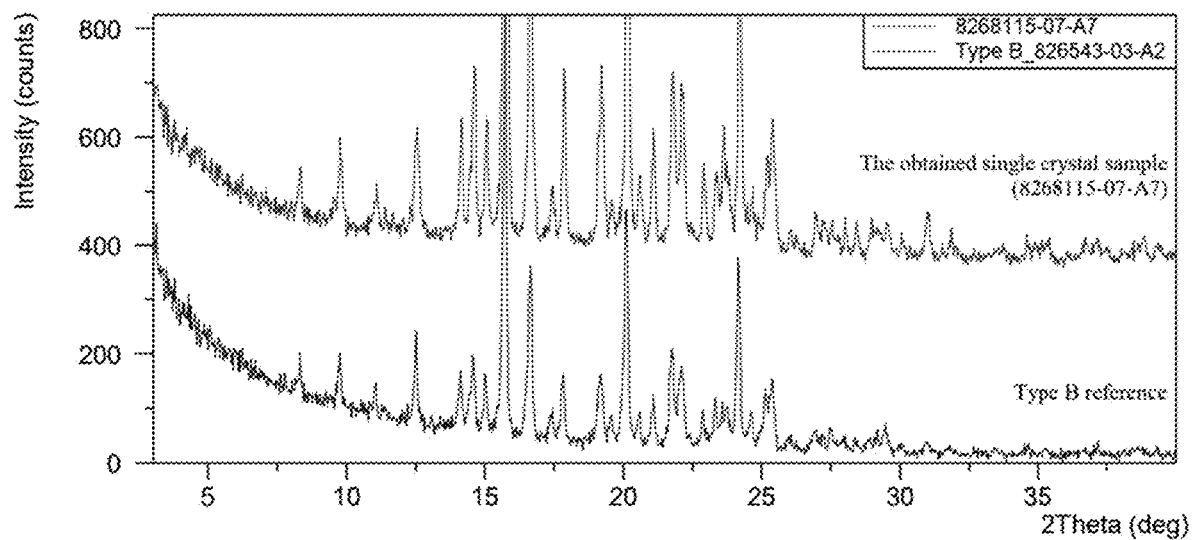
FIG. 34 illustrates XRPD pattern overlay of ABT-301 Type B single crystal and Type B reference.

The single crystal sample (CP ID: 826543-07-A7) of ABT-301 Type B was obtained from 80° C. slow evaporation experiment system. The growth experiment details are elaborated below:

To a 3 mL glass vial were added 5.1 mg ABT-301 Type B sample (CP ID: 826543-39-A) and 0.5 mL acetone. Ultrasonication was applied to accelerate the dissolution of the solid sample, after which the sample suspension was filtered with syringe and syringe filter (0.45 μm PTFE filter membrane). The filtrate was transferred to a clean 4 mL shell vial. The vial was then sealed by ta cap and placed in the 80° C. biochemical incubator. The acetone of the sample solution evaporated slowly at 80° C. After 7 day's evaporation, plank-like single crystals (CP ID: 8268115-07-A7) was obtained, as shown in FIG. 33. The single crystal was then characterized by XRPD. XRPD patterns overlay (FIG. 34) indicated that the experimental XRPD of the obtained single crystal is consistent with that of ABT-301 Type B reference (CP ID: 826543-03-A2).

II. Single Crystal Structure Determination

Single Crystal Structure of Type A

A single crystal of Type A with suitable size and good diffraction quality was cut out and selected from the obtained crystal sample (CP ID: 826543-04-A9) and characterized by single-crystal X-ray diffraction. The single crystal belonged to monoclinic crystal system and the space group was $P2_1/c$. The unit cell dimensions were determined as {a=14.68420 (10) Å, b=44.7093 (3) Å, c=10.46470 (10) Å, α=90°, β=102.5980 (10)°, γ=90°, V=6704.88 (9)}.

Figure 35:
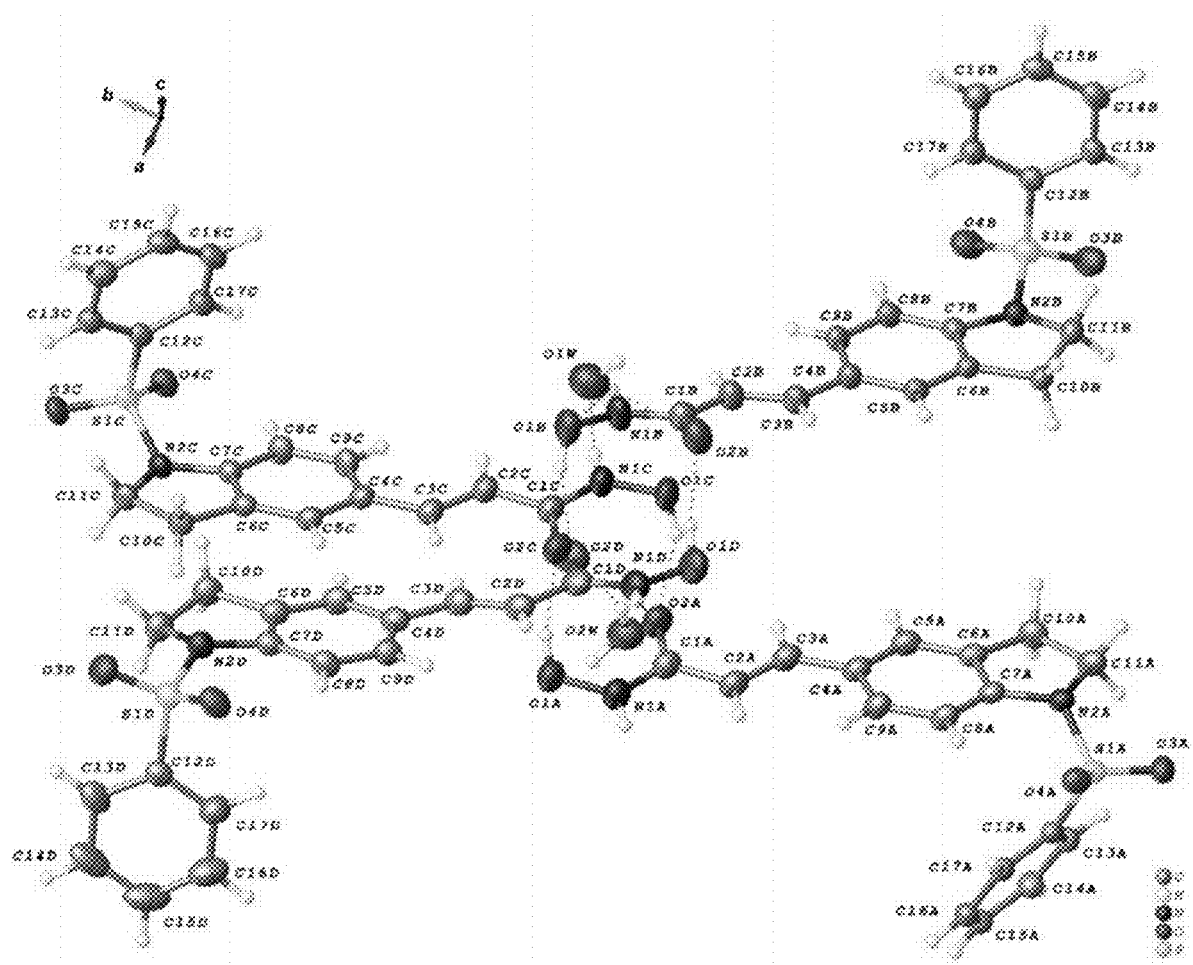
FIG. 35 illustrates the asymmetric unit of the ABT-301 Type A single crystal structure.

Other crystallographic data and the refinement parameters are listed in Table 11. As shown in FIG. 35, the asymmetric unit of the single crystal structure was comprised of four independent ABT-301 molecules and two water molecules, which indicated the single crystal was a hemi-hydrate (the molar ratio of the API/water is 2:1).

TABLE 11

| Sample ID | 826543-04-A9 |
| --- | --- |
| Empirical formula | $C_{17}H_{16}N_2O_4S \cdot 0.5(H_2O)$ |
| Formula weight | 353.38 |
| Temperature | 120.00(10) K |
| Wavelength | Cu/$K_\alpha$ (λ = 1.54184 Å) |
| Crystal system, space group | Monoclinic, $P2_1/c$ |
| Unit cell dimensions | a = 14.68420(10) Å |
| | b = 44.7093(3) Å |
| | c = 10.46470(10) Å |
| | α = 90° |
| | β = 102.5980(10)° |
| | γ = 90° |
| Volume | 6704.88(9) Å$^3$ |
| Z, Calculated density | 16, 1.400 g/cm$^3$ |
| Absorption coefficient | 1.962 mm$^{-1}$ |
| F(000) | 2960.0 |
| Crystal size | 0.21 × 0.09 × 0.06 mm$^3$ |
| 2 Theta range for data collection | 3.952 to 154.588 |
| Limiting indices | −18 ≤ h ≤ 16 |
| | −56 ≤ k ≤ 56 |
| | −13 ≤ l ≤ 13 |
| Reflections collected/ Independent reflections | 151407/14167 [$R_{int}$ = 0.0547, $R_{sigma}$ = 0.0238] |
| Refinement method | Full-matrix least-squares on F$^2$ |
| Completeness | 99.63% |
| Data/restraints/parameters | 14167/0/893 |
| Goodness-of-fit on F$^2$ | 1.040 |
| Final R indices [I ≥ 2sigma(I)] | $R_1$ = 0.0470, w$R_2$ = 0.1244 |
| Final R indices [all data] | $R_1$ = 0.0509, w$R_2$ = 0.1273 |
| Largest diff. peak and hole | 0.63/−0.49 Å$^{-3}$ |

Single Crystal Structure of Type B

Figure 36:
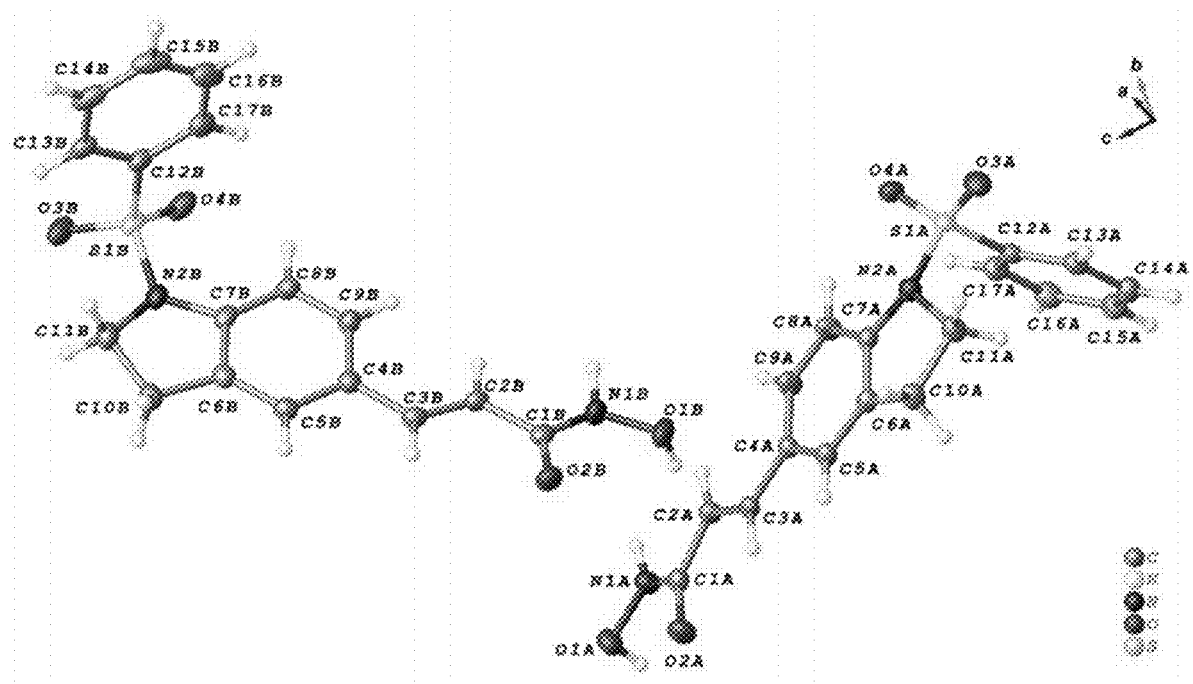
FIG. 36 illustrates the asymmetric unit of the ABT-301 Type B single crystal structure.

A single crystal of suitable size and good diffraction quality was cut out and selected from the obtained Type B single crystal sample (CP ID: 8268115-07-A7) and characterized by single-crystal X-ray diffraction. The structure of the single crystal was determined successfully. The crystal system of the single crystal belonged to orthorhombic crystal system and $P2_12_12_1$ space group. The unit cell dimensions were determined as {a=8.13110 (10) Å, b=9.21070 (10) Å, c=42.5238 (3) Å, α=90°, β=90°, γ=90°, V=3184.74 (6) Å$^3$}. Other crystallographic data and the refinement parameters are listed in Table 12. As shown in FIG. 36, the asymmetric unit of the Type B single crystal structure was comprised of two independent ABT-301 molecules without any water or other solvent molecules, which confirmed that Type B crystal was anhydrate.

TABLE 12

| | |
|---|---|
| Sample ID | 8268115-07-A7 |
| Empirical formula | $C_{17}H_{16}N_2O_4S$ |
| Formula weight | 344.38 |
| Temperature | 120.00(10) K |
| Wavelength | Cu/$K_\alpha$ ($\lambda$ = 1.54184 Å) |
| Crystal system, space group | Orthorhombic, $P2_12_12_1$ |
| Unit cell dimensions | a = 8.13110(10) Å |
| | b = 9.21070(10) Å |
| | c = 42.5238(3) Å |
| | $\alpha = 90°$ |
| | $\beta = 90°$ |
| | $\gamma = 90°$ |
| Volume | 3184.74(6) Å$^3$ |
| Z, Calculated density | 8, 1.436 g/cm$^3$ |
| Absorption coefficient | 2.027 mm$^{-1}$ |
| F(000) | 1440.0 |
| Crystal size | 0.13 × 0.055 × 0.045 mm$^3$ |
| 2 Theta range for data collection | 4.156 to 154.52 |
| Limiting indices | $-9 \leq h \leq 10$ |
| | $-11 \leq k \leq 11$ |
| | $-53 \leq l \leq 53$ |
| Reflections collected/ Independent reflections | 20012/6540 [$R_{int}$ = 0.0219, $R_{sigma}$ = 0.0233] |
| Refinement method | Full-matrix least-squares on F$^2$ |
| Completeness | 100.00% |
| Data/restraints/parameters | 6340/0/449 |
| Goodness-of-fit on F$^2$ | 1032 |
| Final R indices [I ≥ 2sigma(I)] | $R_1$ = 0.0270, $wR_2$ = 0.0702 |
| Final R indices [all data] | $R_1$ = 0.0276, $wR_2$ = 0.0706 |
| Largest diff. peak and hole | 0.34/−0.24 Å$^{-3}$ |
| Flack parameter | 0.128(4) |

Methods

Single Crystal Diffraction Data Collection

The suitable single crystals with suitable size and good diffraction quality were cut out and selected from the obtained single crystals and wrapped with Paratone-N (an oil based cryoprotectant). The selected single crystal was mounted on a Cryoloop and fixed on the goniometer head with a random orientation. The single crystal was immersed in a stream of nitrogen at 120 K. Preliminary examination and data collection were performed on a Rigaku XtaLAB Synergy R (Cu/Kα X-ray radiation, $\lambda$=1.54184 Å) diffractometer at 120 K.

For the Type A single crystal sample (CP ID: 826543-04-A9), cell parameters and orientation matrixes for data collection were retrieved and refined (T-vector algorithm) by CrysAlisPro (version: 1.171.42.89a) software using the setting angles of 77940 reflections in the range 1.9580°<θ<77.1750°. The data were collected to a minimum diffraction angle (θ) of 1.976° and a maximum diffraction angle (θ) of 77.294°. The completeness of data collection is 99.63%. The mean I/o of the collected data is 42.0 and the highest resolution is truncated at 0.79 Å.

For the Type B single crystal sample (CP ID: 8268115-07-A7), cell parameters and orientation matrixes for data collection were retrieved and refined (T-vector algorithm) by CrysAlisPro (version: 1.171.42.89a) software using the setting angles of 15573 reflections in the range 4.1250°<θ<77.0180°. The data were collected to a minimum diffraction angle (θ) of 2.078° and a maximum diffraction angle (θ) of 77.260°. The completeness of data collection is 100.00%. The mean I/o of the collected data is 43.0 and the highest resolution is truncated at 0.79 Å.

Single Crystal Diffraction Data Reduction

Frames were integrated with CrysAlisPro (version: 1.171.42.89a). Lorentz and polarization corrections were applied to the data.

For the Type A single crystal sample (CP ID: 826543-04-A9), a total of 151407 reflections in the range 1.976°<θ<77.294° were collected, of which 14167 were unique. An empirical absorption correction was performed using CrysAlisPro (version: 1.171.42.89a) using spherical harmonicsas implemented in SCALE3 ABSPACK. The absorption coefficient μ of this material is 1.962 mm$^{-1}$ at this wavelength ($\lambda$=1.54184 Å) and the minimum and maximum transmissions are 0.81852 and 1.00000, respectively. Intensities of equivalent reflections were averaged. The average agreement factor of all equivalent reflections ($R_{int}$) was 5.47% based on intensity.

For the Type B single crystal sample (CP ID: 8268115-07-A7), a total of 20012 reflections in the range 2.078°<θ<77.260° were collected, of which 6540 were unique. An empirical absorption correction was performed using CrysAlisPro (version: 1.171.42.89a) using spherical harmonicsas implemented in SCALE3 ABSPACK. The absorption coefficient μ of this material is 2.027 mm$^{-1}$ at this wavelength (2=1.54184 Å) and the minimum and maximum transmissions are 0.71191 and 1.00000, respectively. Intensities of equivalent reflections were averaged. The average agreement factor of all equivalent reflections ($R_{int}$) was 2.19% based on intensity.

Methods of Single Crystal Structure Solving and Refinement

The two single crystal structures were solved in the space group P1 with the ShelXT (version: 2018/2) structure solution program using Intrinsic Phasing method and refined with ShelXL (Version 2018 3) refinement package using full-matrix least-squares on F2 contained in Olex2 (version: 1.5). All nonhydrogen atoms were refined anisotropically.

For the Type A single crystal sample (CP ID: 826543-04-A9), hydrogen atoms were calculated geometrically and refined using the riding model.

For the Type B single crystal sample (CP ID: 8268115-07-A7), the nitrogen-bonding or oxygenbonding hydrogen atoms were found from Fourier map, and refined isotropically and positionally. Other hydrogen atoms were calculated geometrically and refined using the riding model.

Software for Calculation of XRPD Pattern

The calculated XRPD pattern was generated for Cu radiation using Mercury (version: 4.3.1) program and the atomic coordinates, space group, and unit cell parameters from the single crystal structure.

Software for Single Crystal Structure Visualization

The crystal structure representations were generated by Olex2 (version: 1.5) and Mercury (version: 4.3.1). The thermal ellipsoids drawing was generated by ORTEP-III2 (version: 2014.1) software.

Instruments and Parameters

The PLM images of obtained single crystal samples were captured using OLYMPUS SZX-7 stereoscopic microscope. The single crystal X-ray diffraction data were collected at 120 K with Rigaku XtaLAB Synergy R (Cu/Kα radiation, $\lambda$=1.54184 Å) diffractometer. The XRPD data were collected by PANalytical Empyrean X-ray diffractometer. The SCXRD instrument and the XRPD instrument parameters are shown in Table 13 and Table 14, respectively.

TABLE 13

| Instrument | Rigaku XtaLAB SynergyR |
|---|---|
| X-ray sources generator | PhotonJet R (Cu) X-ray Source (Cu/Kα: 1.54184 Å) |
| Detector | Hypix 6000C detector |
| Gloniometer | Four-circle Kappa Goniometer |
| Low Temperature Devices | Cryostream-800 Pluse (80~500 K) |
| Software package | CrysAlisPro |

TABLE 14

| Instrument | PANalytical Empyrean |
|---|---|
| Model | Reflection mode Cu/Kα, |
| X-Ray wavelength | Kα$_1$(Å): 1.540598<br>Kα$_2$(Å): 1.544426<br>Kα$_2$/Kα$_1$ intensity ratio: 0.50 |
| X-Ray tube setting | 45 kV, 40 mA |
| Divergence slit (°) | 1/8 |
| Scan mode | Continuous |
| Scan range (°2Theta) | 3~40 |
| Counting time (s) | 96.390 |
| Step size (°2Theta) | 0.0263 |
| Test time (h:m:s) | About 5 min |

Example 4

Solid Stability Evaluation

Polymorph screening was performed in Example 2, hydrate Type A and anhydrate Type B were discovered. The purpose of Example 4 is to perform evaluation for ABT-301 Type A and B to identify a suitable crystalline form for further development. Based on the results of polymorph screening, the inter-conversion relationship between Type A and Type B were related to the water content (or water activity) and temperature. Therefore, the two forms were selected for solid stability evaluation to identify a lead form for further development. Amorphous was also selected for evaluation as reference.

I. The Characterization Results

Figure 37:
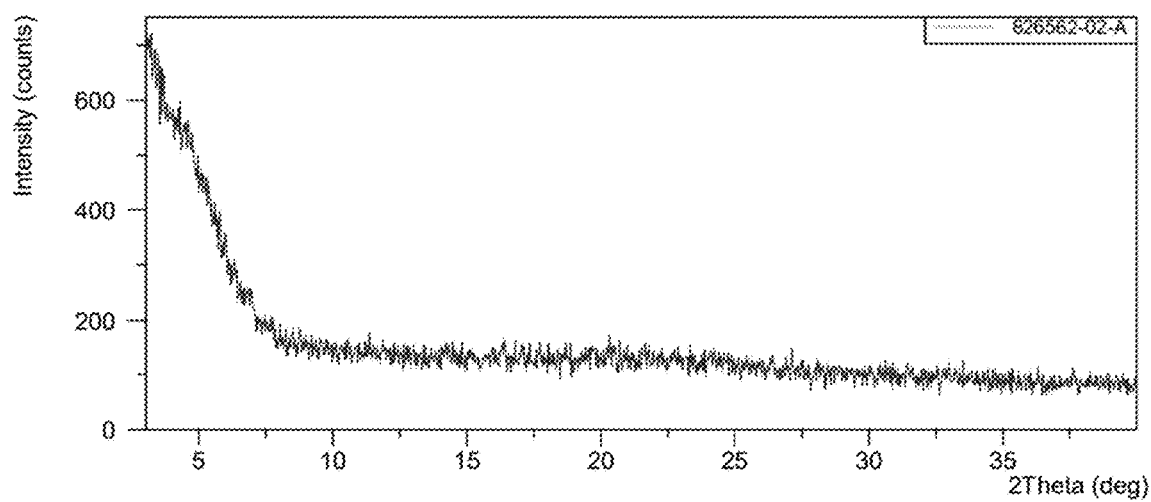
FIG. 37 illustrates XRPD pattern overlay of re-prepared amorphous (826562-02-A)
Figure 38:
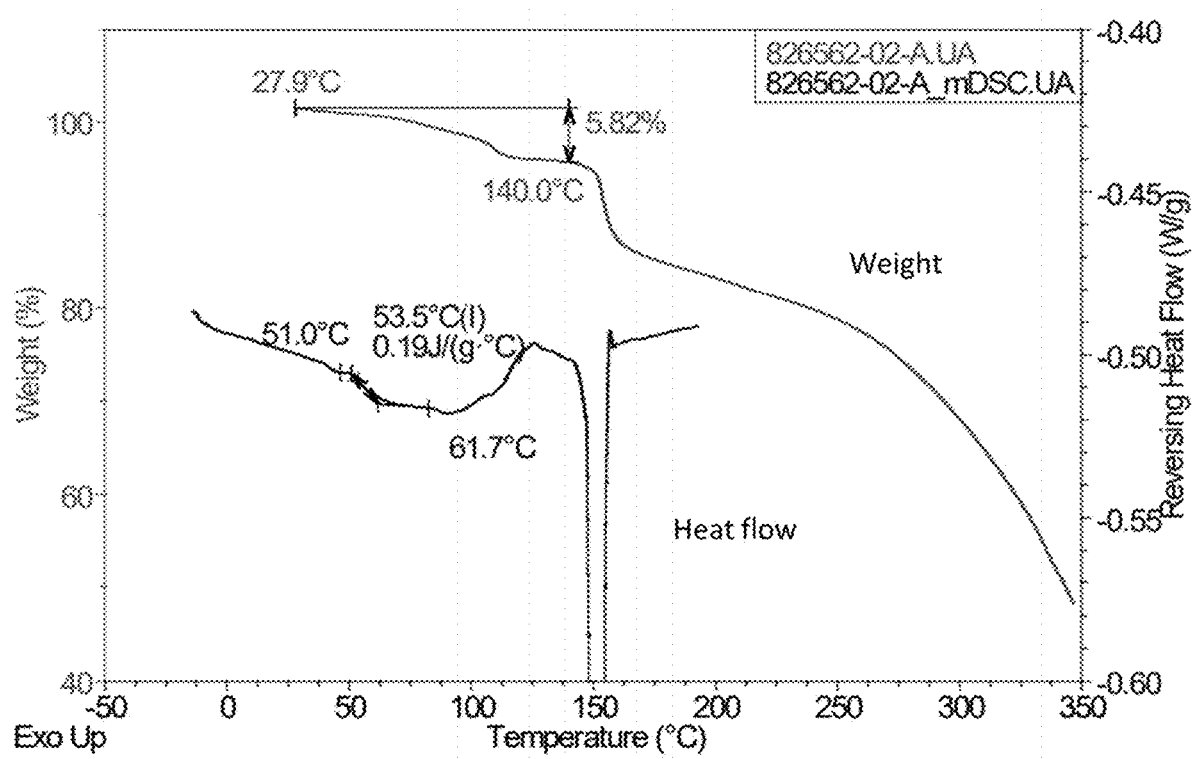
FIG. 38 illustrates TGA/mDSC curves of re-prepared amorphous (826562-02-A)
Figure 39:
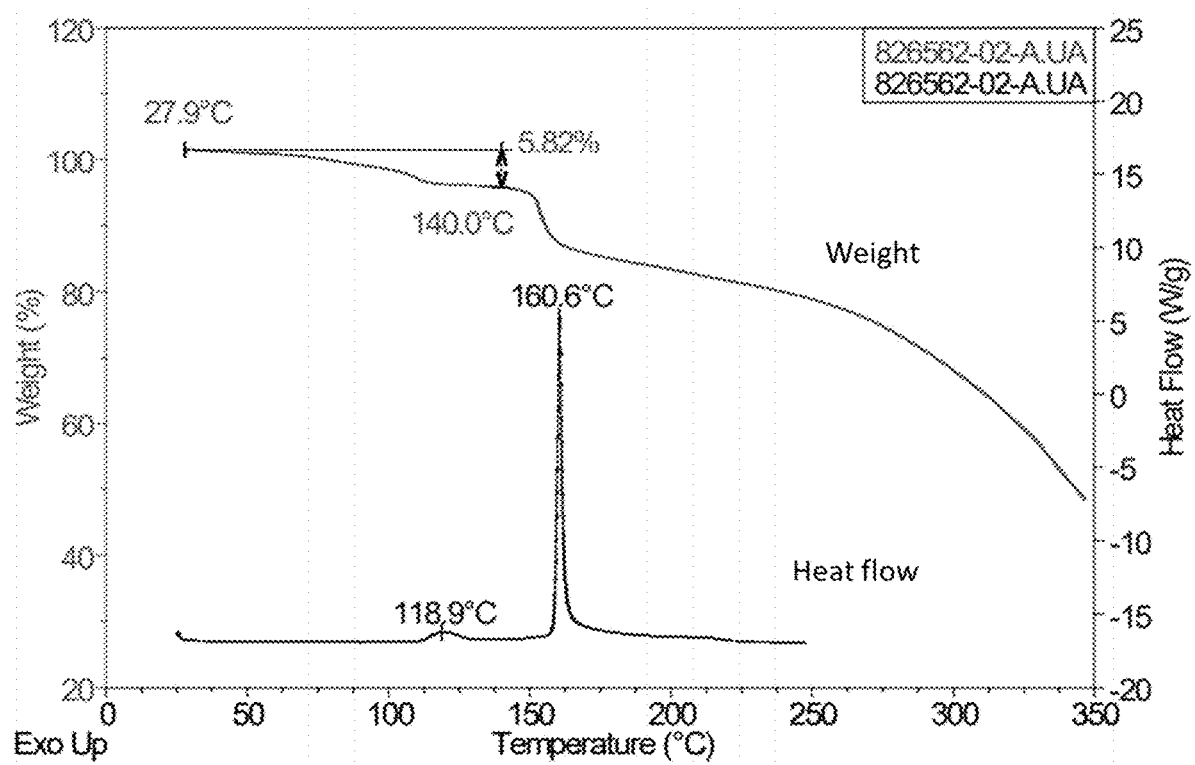
FIG. 39 illustrates TGA/DSC curves of re-prepared amorphous (826562-02-A)

The characterization results of Type A and Type B have been shown in Example 2. As for amorphous, the re-preparation was performed via different methods, including grinding, rotary evaporation, reverse anti-solvent addition and freeze drying. For example, amorphous re-preparation was performed via rotary evaporation under the low ambient humidity (20% RH). Amorphous (826562-02-A) was obtained by rotary evaporation of ~156 mg Type A (826543-01-A) in Acetone. XRPD result (FIG. 37) showed that amorphous was obtained. This sample was used for solid stability. TGA/mDSC results were shown in FIG. 38. TGA result showed a weight loss of 5.82% at up to 150° C. mDSC result showed a glass transition temperature at 53.5° C. (inflection temperature). DSC result (FIG. 39) showed two exotherms at 118.9 and 160.6° C. (peak) were observed.

II. Solid Stability

Type A/B were stored under the conditions of 60° C., 25° C./60% RH, 25° C./92.5% RH and 40° C./75% RH for 1/2/4 weeks for solid stability evaluation. Amorphous was stored under the conditions of 25° C./60% RH and 40° C./75% RH for 1/2/4 weeks for solid stability evaluation. The physical and chemical stability were evaluated by X-ray powder diffraction (XRPD), thermo gravimetric analysis (TGA)/Karl Fischer (KF), differential scanning calorimetry (DSC)/modulated differential I scanning calorimetry (mDSC), high performance liquid chromatography (HPLC) purity and assay, respectively.

The results were summarized from Table 15 to Table 16. Solid stability results showed that no form change, or obvious HPLC purity change were observed for both Type A and Type B after solid stability for 4 weeks. Amorphous converted to Type A after solid stability evaluation and no obvious HPLC purity change was observed after solid stability for 4 weeks.

TABLE 15

| Starting Material (826543-) | Condition | Time | Form | TGA weight loss (%, 150° C.) | KF (water content) | DSC endotherm* ° C., peak) | HPLC purity (Area %) | Assay (%) |
|---|---|---|---|---|---|---|---|---|
| Type A 01-A | Initial | — | Type A | 3.77 | 2.8220% | 118.7, 125.5, 166.1* | 99.84 | 95.6 |
| | 60° C. | 1 week | Type A | 3.36 | NA | 119.1, 125.1, 165.3* | 99.83 | 96.2 |
| | | 2 weeks | Type A | 3.06 | NA | 113.5, 164.6* | 99.76 | 95.0 |
| | | 4 weeks | Type A | 5.09 | 4.3786% | 115.7, 165.6* | 99.82 | 95.7 |
| | 25° C./ 60% RH | 1 week | Type A | 4.14 | NA | 117.2, 124.5, 165.5 | 99.85 | 96.4 |
| | | 2 weeks | Type A | 7.10 | NA | 113.6, 165.2* | 99.83 | 94.7 |
| | | 4 weeks | Type A | 3.93 | 2.8030% | 114.9, 164.7* | 99.84 | 96.4 |
| | 25° C./ 92.5% RH | 1 week | Type A | 3.86 | NA | 115.5, 164.4* | 99.85 | 96.3 |
| | | 2 weeks | Type A | 6.70 | NA | 114.2, 164.7* | 99.84 | 95.6 |
| | | 4 weeks | Type A | 4.03 | 3.1154% | 114.3, 164.8* | 99.85 | 96.5 |
| | 40° C./ 75% RH | 1 week | Type A | 4.15 | NA | 117.1, 124.4, 165.6 | 99.84 | 96.6 |
| | | 2 weeks | Type A | 4.06 | NA | 115.3, 164.6* | 99.84 | 95.6 |
| | | 4 weeks | Type A | 3.88 | 4.1509% | 115.1, 164.7* | 99.85 | 96.1 |
| | Initial | — | Type B | 0.74 | 0.5387% | 166.2* | 99.85 | 96.8 |
| | 60° C. | 1 week | Type B | 2.57 | NA | 163.9* | 99.84 | 98.0 |
| | | 2 weeks | Type B | 2.44 | NA | 167.6* | 99.80 | 96.5 |
| | | 4 weeks | Type B | 3.12 | 1.9894% | 170.0* | 99.76 | 97.9 |
| | 25° C./ 60% RH | 1 week | Type B | 0.64 | NA | 164.2* | 99.85 | 97.8 |
| | | 2 weeks | Type B | 0.95 | NA | 168.2* | 99.85 | 96.8 |
| | | 4 weeks | Type B | 1.65 | 2.0658% | 168.6* | 99.86 | 98.2 |
| | 25° C./ 92.5% RH | 1 week | Type B | 0.35 | NA | 163.5* | 99.85 | 97.9 |
| | | 2 weeks | Type B | 2.98 | NA | 167.4* | 99.85 | 96.8 |
| | | 4 weeks | Type B | 3.52 | 1.8514% | 167.6* | 99.85 | 98.1 |

TABLE 15-continued

| Starting Material (826543-) | Condition | Time | Form | TGA weight loss (%, 150° C.) | KF (water content) | DSC endotherm* (° C., peak) | HPLC purity (Area %) | Assay (%) |
|---|---|---|---|---|---|---|---|---|
| | 40° C./ 75% RH | 1 week | Type B | 2.46 | NA | 164.9* | 99.85 | 97.6 |
| | | 2 weeks | Type B | 1.84 | NA | 167.9* | 99.84 | 97.1 |
| | | 4 weeks | Type B | 0.71 | 0.8491% | 167.1* | 99.85 | 97.8 |

*Exotherm.

TABLE 16

| Starting Material (826562-) | Condition | Time | Form | TGA weight loss (%, 150° C.) | Method | DSC endotherm (° C., peak) | HPLC purity (Area %) | Assay (%) |
|---|---|---|---|---|---|---|---|---|
| Amorphous 02-A | Initial | — | Amorphous | 5.82 | mDSC | 53.5* | 99.84 | 91.5 |
| | | | | | DSC | 118.9*, 160.6# | | |
| | 25° C./ 60% RH | 1 week | Type A | 6.95 | mDSC | 88.1, 98.3*, 154.5# | 99.71 | 91.3 |
| | | | | | DSC | 106.8, 119.3*, 163.4# | | |
| | | 2 weeks | Type A | 6.46 | mDSC | 90.2, 99.0*, 154.4# | 99.76 | 92.2 |
| | | | | | DSC | 107.1, 118.9*, 163.6# | | |
| | | 4 weeks | Type A | 6.20 | mDSC | 95.1, 108.2*, 153.2# | 99.81 | 90.7 |
| | | | | | DSC | 110.0, 118.0*, 162.9# | | |
| | 40° C./ 75% RH | 1 week | Type A | 6.20 | mDSC | 98.0, 110.5*, 151.9# | 99.75 | 91.5 |
| | | | | | DSC | 107.8, 121.2*, 162.0# | | |
| | | 2 weeks | Type A | 3.52 | mDSC | 90.7, 107.6*, 152.3# | 99.78 | 92.1 |
| | | | | | DSC | 109.6, 121.5*, 162.0# | | |
| | | 4 weeks | Type A | 4.78 | mDSC | 92.3, 108.4*, 152.1# | 99.84 | 90.6 |
| | | | | | DSC | 109.6, 121.4*, 161.9# | | |

*Inflection temperature.
Exotherm.

Methods

XRPD, TGA, DSC and KF in this example are under the same conditions with those described in Example 2.

PLM

PLM images were captured on Axio Lab. A1 upright microscope, purchased from Carl Zeiss German.

mDSC

Parameters for mDSC test are as below:

TABLE 17

| Parameters | mDSC |
|---|---|
| Method | Conventional MDSC |
| Sample pan | Aluminum, crimped |
| Temperature | −20° C.-Target temperature |
| Heating rate | 3° C./min |
| Modulation temperature amplitude +/− | 1° C. |
| Modulation | 60 s |
| Purge gas | $N_2$ |

Freeze Dryer

Freeze drying was performed on SCIENTZ-30FG/A freeze dryer.

HPLC/IC

Agilent 1260 were utilized and detailed chromatographic conditions are listed in

TABLE 18

| Parameters | Agilent 1260 with VWD detector | |
|---|---|---|
| Column | Gemini C18 110A, 250 × 4.6 mm, 5 μm | |
| | A: 0.1% $H_3PO_4$ in $H_2O$ | |
| | B: MeOH | |
| | Time (min) | % B |
| Mobile phase | 0.0 | 45 |
| | 30.0 | 60 |
| | 35.0 | 60 |
| | 35.5 | 45 |
| | 40.0 | 45 |
| Run time | 40.0 min | |
| Flow rate | 1.0 mL/min | |
| Injection volume | 8 μL | |
| Detector wavelength | 300 nm | |
| Column temperature | 30° C. | |
| Sampler temperature | RT | |
| Diluent | ACN/$H_2O$ (1:1, v/v) | |

Furthermore, a long-term stability test and an accelerated stability test of Type A (in the form of powder) are executed, and the results thereof are shown in Table 19 and Table 20, respectively. More specifically, for the long-term stability test, the packaging and storage condition: package in double PE bags with silica gel in an aluminum bag and in a paper drum; sample quantity: 0.6 g; temperature: 25±2° C.; % relative humidity: 60±5%; frequency of analysis: 0, 1, 2, 3, 6, 9, 12, 18, 24, 36, 48 and 60 months; duration: 60 months. As for the accelerated stability test, the packaging and storage condition: package in double PE bags with silica gel in an aluminum bag and in a paper drum; sample quantity: 0.6 g; temperature: 40±2° C.; % relative humidity: 75±5%; frequency of analysis: 0, 1, 2, 3 and 6 months; duration: 6 months.

TABLE 19

| | | | | Related substance (HPLC) | | | |
|---|---|---|---|---|---|---|---|
| Storage time (Months) | Appearance | Identification, USP<197K> Infrared absorption | Water content (KF) (NMT 4.0%) | ABT-301 dimer (a/a %) (NMT 0.5%) | Individual unknown Impurity (NMT 0.4%) | Total Impurities (NMT 1.0%) | Assay (HPLC) (98.0%~102.0%) (anhydrous basis) |
| 0 | Pale white powder | Conform to reference spectrum | 2.6 | 0 | 0.03 | 0.1 | 101.6 |
| 1 | Pale white powder | Conforin to reference spectrum | 2.6 | 0 | 0.05 | 0.1 | 100.3 |
| 2 | Pale white powder | Conform to reference spectrum | 2.6 | 0 | 0.05 | 0.1 | 100.6 |
| 3 | Pale white powder | Conform to reference spectrum | 2.6 | 0 | 0.07 | 0.1 | 101.4 |
| 6 | Pale white powder | Conform to reference spectrum | 2.6 | 0 | 0.05 | 0.1 | 100.2 |
| 9 | Pale white powder | Conform to reference spectrum | 2.9 | 0 | 0.06 | 0.1 | 100.6 |
| 12 | Pale white powder | Conform to reference spectrum | 2.6 | 0 | 0.09 | 0.2 | 100.4 |
| 18 | Pale white powder | Conform to reference spectrum | 2.8 | 0 | 0.07 | 0.1 | 100.0 |
| 24 | Pale white powder | Confonn to reference spectrum | 2.7 | 0 | 0.03 | 0.1 | 99.8 |
| 36 | Pale wlite powder | Conform to reference spectrum | 2.6 | 0 | 0.08 | 0.1 | 100.1 |
| 48 | Pale white powder | Conform to reference spectrum | 2.6 | 0 | 0.08 | 0.1 | 100.4 |
| 60 | Pale white powder | Conform to reference spectrum | 2.6 | ND | 0.08 | 0.1 | 100.5 |

TABLE 20

| | | | | Related substance (HPLC) | | | |
|---|---|---|---|---|---|---|---|
| Storage time (Months) | Appearance | Identification, USP<197K> Infrared absorption | Water content (KF) (NMT 4.0%) | ABT-301 dimer (a/a %) (NMT 0.5%) | Individual unknown Impurity (NMT 0.4%) | Total Impurities (NMT 1.0%) | Assay (HPLC) (98.0%~102.0%) (anhydrous basis) |
| 0 | Pale white powder | Conforin to reference spectrum | 2.6 | 0.03 | 0.03 | 0.08 | 101.6 |
| 1 | Pale white powder | Conform to reference spectrum | 2.6 | 0.03 | 0.05 | 0.12 | 100.2 |
| 2 | Pale white powder | Conforin to reference spectrum | 2.6 | 0.03 | 0.03 | 0.09 | 101.2 |
| 3 | Pale white powder | Conform to reference spectrum | 2.6 | 0.03 | 0.06 | 0.11 | 101.8 |
| 6 | Pale white powder | Conform to reference spectrum | 2.6 | 0.03 | 0.06 | 0.13 | 99.8 |

Example 5

Composition and Stability Study of ABT-301 Capsules

I. Formula

In this section, the stability of the crystalline form of ABT-301 as active pharmaceutical ingredients (API) is tested from various aspects. First of all, a pharmaceutical composition, more particularly, a capsule comprising 50 mg of Type A form of ABT-301 as API is presented, and the representative formula is shown in Table 21.

TABLE 21

| Ingredient | Unit Formula (mg) | % w/w |
|---|---|---|
| ABT-301 drug substance | 50 | 5.882 |
| Polysorbate 80 | 200 | 23.53 |
| Propylene glycol | 100 | 11.76 |
| Polyoxyl (35) castor oil | 500 | 58.82 |
| Total Capsule Fill Weight | 850 | 100 |
| Gelatin 160 | 235 | 58.75 |
| Glycerin | 105 | 26.25 |
| Titanium dioxide | 2.5 | 0.615 |
| Iron oxide black | 0.2 | 0.05 |
| Purified water | 57.3 | 14.325 |
| Total Capsule Shell Weight | 400 | 100 |
| Medium-chain Triglycerides | q.s.* | |

*q.s. stands for quantum satis. Medium-chain triglycerides can be removed during the process.

II. Manufacturing Process

The manufacturing process of ABT-301 Capsules, 50 mg are briefly described as follows:

Step 1: Preparation of Gel Mass

Charge purified water to a glue digester, then glycerin is slowly charged, and stir for about 10 minutes. Heat to 65° C. under stirring, then charge gelatin 160 until the gelatin is melted. Start vacuuming and maintain the vacuum pressure less than-0.06 MPa with stirring until the color of gel becomes a brown solution. Sample for viscosity test. Charge dispensed titanium dioxide, iron oxide black, and purified water to a suitable container and homogenized using a homogenizer for about 25-30 minutes. Charge the mixture of titanium dioxide and iron oxide black suspension to the above glue digester during stirring, and vacuum to less than-0.06 MPa. Sample for viscosity and loss on drying test. Keep the gelatin solution at 60° C.

Step 2: Preparation of Content Mixture

Charge dispensed polyoxyl (35) castor oil, polysorbate 80, and propylene glycol to a jacketed vessel and protect from light. Blend with stirring at about 50° C. for about 25 minutes. Charge part of the dispensed ABT-301 drug substance to part of the above heated solution and stir with homogenizer for about 2-5 minutes. Repeat the above operations until all the dispensed ABT-301 drug substance is homogenized. After standing overnight, sample for blend uniformity.

Step 3: Encapsulation

Fill the content mixture from step 2 into capsule shells from step 1 using a soft capsule machine. Use medium-chain triglycerides to lubricate the shells during encapsulation (refer to the encapsulation parameters in Table 22). Samples for individual filling weight per soft capsule and ribbon thickness test at appropriate intervals throughout the encapsulation operation.

TABLE 22

| Encapsulation parameters | Suggested value range |
|---|---|
| Mould speed | 1.5 (1.3-3.0) rpm |
| Left/Right ribbon wheel | 0.45 (0.4-1.0) rpm |
| Left/Right gelatin box temperature | 60 (55-65)° C. |
| Hopper temperature | 42.0 (35-45)° C. |
| Spray body (Injection) temperature | 43.0 (35-45)° C. |
| Refrigeration temperature | 20 (18-22)° C. |
| Tumbler drying time | 1.5 (0.5-3.0) h |
| Ribbon thickness | 0.80 (0.70-0.90) mm |

Step 4: Drying

Polish and shape the soft capsules in a rotary tumbler dryer for 1.5 hour at a temperature of 15-25° C. and humidity of less than 35% RH. Sample for hardness and loss on drying test.

Step 5: Packaging

ABT-301 capsules, 50 mg, are packaged in a 120 mL HDPE (high-density polyethylene) bottle, containing two 1 g desiccants, about 5 cm of pharma coil, then enclosed with a 38 mm PP (polypropylene) cap, each bottle contains 35 capsules.

III. Stability Study

In this section, the stability of the ABT-301 Capsules, 50 mg described above under long-term storage condition (5±3° C.) are examined, and the results thereof are shown in Table 23 and Table 24.

TABLE 23

| Testing Items | Acceptance Criteria | Initial | 1 M | 3 M | 6 M |
|---|---|---|---|---|---|
| Description | An oblong-shaped and gray color soft capsule | An oblong-shaped and gray color soft capsule | An oblong-shaped and gray color soft capsule | An oblong-shaped and gray color soft capsule | An oblong-shaped and gray color soft capsule |
| Assay | 90.0%-110.0% | 100.6% | 100.4% | 99.3% | 98.9% |
| Degradation Products | MPT0E028 dimer ≤0.4% | 0.1% | 0.11% | 0.1% | 0.09% |
| | Individual unknown impurity ≤0.4% | 0.0% | 0.02% | 0.0% | 0.03% |
| | Total impurities ≤1.0% | 0.3% | 0.34% | 0.5% | 0.32% |
| Microbial Limits | Total Aerobic Microbial Count (TAMC) ≤1000 cfu/g | <100 cfu/g | N/A | N/A | N/A |
| | Total Combined Yeasts and Molds Count (TYMC) ≤100 cfu/g | <100 cfu/g | N/A | N/A | N/A |
| | *Escherichia coli*: Not present in 1 g | Not present in 1 g | N/A | N/A | N/A |

TABLE 24

| Testing Items | Acceptance Criteria | Initial | 1 M | 3 M | 6 M |
|---|---|---|---|---|---|
| Description | An oblong-shaped and gray color soft capsule | An oblong-shaped and gray color soft capsule | An oblong-shaped and gray color soft capsule | An oblong-shaped and gray color soft capsule | An oblong-shaped and gray color soft capsule |
| Assay | 90.0%-110.0% | 97.8% | 102.9% | 101.5% | 99.5% |
| Degradation Products | MPT0E028 dimer ≤0.4% | 0.13% | 0.12% | 0.13% | 0.13% |
| | Individual unknown impurity ≤0.4% | 0.07% | 0.19% | 0.08% | 0.11% |
| | Total impurities ≤1.0% | 0.4% | 1.0% | 0.51% | 0.81% |
| Microbial Limits | Total Aerobic Microbial Count (TAMC) ≤1000 cfu/g | N/A | <100 cfu/g | <100 cfu/g | <100 cfu/g |
| | Total Combined Yeasts and Molds Count (TYMC) ≤100 cfu/g | N/A | <100 cfu/g | <100 cfu/g | <100 cfu/g |
| | *Escherichia coli*: Not present in 1 g | N/A | Not present in 1 g | Not present in 1 g | Not present in 1 g |

The accelerated stability data of the ABT-301 Capsules, 50 mg described above are examined, and the results thereof are shown in Table 25.

TABLE 25

| Testing Items | Acceptance Criteria | Initial | 1 M | 3 M | 6 M |
|---|---|---|---|---|---|
| Description | An oblong-shaped and gray color soft capsule | An oblong-shaped and gray color soft capsule | An oblong-shaped and gray color soft capsule | An oblong-shaped and gray color soft capsule | An oblong-shaped and gray color soft capsule |
| Assay | 90.0%-110.0% | 100.6% | 98.8% | 96.8% | 99.0% |
| Degradation Products | MPT0E028 dimer ≤0.4% | 0.1% | 0.16% | 0.2% | 0.28% |
| | Individual unknown impurity ≤0.4% | 0.0% | 0.02% | 0.0% | 0.08% |
| | Total impurities ≤1.0% | 0.3% | 0.44% | 0.7% | 0.99% |
| Microbial Limits | Total Aerobic Microbial Count (TAMC) ≤1000 cfu/g | <100 cfu/g | N/A | N/A | <100 cfu/g |
| | Total Combined Yeasts and Molds Count (TYMC) ≤100 cfu/g | <100 cfu/g | N/A | N/A | <100 cfu/g |
| | *Escherichia coli*: Not present in 1 g | Not present in 1 g | N/A | N/A | Not present in 1 g |

Example 6

Pharmacokinetics Study

In this section, the pharmacokinetics of different dosage forms of the ABT-301 are examined and compared. More specifically, the objective of this study is to evaluate the pharmacokinetics of ABT-301 in Beagle dogs following single dose of ABT-301 different dosage forms via oral and intravenous administration. Animals for oral administration were fasted overnight prior to dosing and 4 hours post-dose and drinking water was controlled within 5 minutes post-dose and allowed ad libitum throughout the study period.

The experiments were designed as crossover study (three periods). Three male Beagle dogs were used for testing ABT-301 different dosages. In period I, animals were administrated for ABT-301 oral capsule (2 capsules, 100 mg) via oral administration; In period II, animals were administrated for ABT-301 oral suspension (50 mL, 100 mg) via oral administration; In period III, animals were administrated for ABT-301 IV solution (10 mL, 15 mg) via intravenous injection. Washout time between every period is 144 hours at least.

After treatment, the blood was drawn at appropriate time and followed by centrifugation. The plasma fraction was collected and the plasma concentration of ABT-301 was determined by LC/MS/MS. The plasma concentration-time data were used to calculate the pharmacokinetic parameters of ABT-301.

Mean ABT301 $AUC_{(0-t)}$ and $AUC_{(0-\infty)}$ of ABT301 oral capsule 100 mg were 618.6±8.4 ng×h/mL and 622.9±7.2 ng×h/mL, respectively. The mean $C_{max}$ was 538.435±11.352 ng/ml. The mean residence time (MRT), the terminal half-life ($T_{1/2}$) and the $T_{max}$ were 1.91±0.24 h, 3.84±3.47 h and 1.00±0.00 h, respectively. The mean clearance (CL/F) and volume distribution ($V_d/F$) were 160.6±1.8 L/h and 891.0±809.7 L, respectively.

Mean ABT301 $AUC_{(0-t)}$ and $AUC_{(0-\infty)}$ of ABT301 oral suspension 100 mg were 120.8±24.8 ng×h/mL and 132.0±27.2 ng×h/mL, respectively. The mean $C_{max}$ was 41.992±4.872 ng/mL. The mean residence time (MRT), the terminal half-life ($T_{1/2}$) and the $T_{max}$ were 6.57±3.26 h, 5.35±2.88 h and 0.83±0.29 h, respectively. The mean clearance (CL/F) and volume distribution ($V_d/F$) were 781.5±176.7 L/h and 5664.5±2567.8 L, respectively.

Mean ABT301 $AUC_{(0-t)}$ and $AUC_{(0-\infty)}$ of ABT301 IV formulation 15 mg were 294.6±22.5 ng×h/mL and 295.6±23.1 ng×h/mL, respectively. The mean $C_{max}$ and $C_0$ was 480.610±82.087 ng/mL and 601.327±135.844 ng/ml, respectively. The mean residence time (MRT), the terminal half-life ($T_{1/2}$) and the $T_{max}$ were 0.583±0.015 h, 0.805±0.298 h and 0.083±0.00 h, respectively. The mean clearance (CL/F) and volume distribution ($V_d$/F) were 51.0±4.1 L/h and 58.3±17.8 L, respectively Summary table of pharmacokinetic parameters are listed in Table 26. The bioavailability (F %) of ABT-301 oral capsule & oral suspension were 31.7±2.4% and 6.7±1.4%, respectively. These results indicated the improved formulation of oral capsule was much better than oral suspension.

TABLE 26

|  | ABT301 IV/solution 15 mg | ABT301 Oral/suspension 100 mg | ABT301 Oral/capsule 100 mg |
|---|---|---|---|
| $T_{max}$ (h) | 0.083 ± 0.00 | 0.83 ± 0.29 | 1.00 ± 0.00 |
| $C_{max}$ (ng/mL) | 480.610 ± 82.087 | 41.992 ± 4.872 | 538.435 ± 11.352 |
| $C_{max}$/dose | 32.041 ± 5.472 | 0.420 ± 0.049 | 5.384 ± 0.114 |
| $AUC_{0-\infty}$ (h * ng/mL) | 295.6 ± 23.1 | 132.0 ± 27.2 | 622.9 ± 7.2 |
| $AUC_{0-\infty}$/dose | 19.7 ± 1.5 | 1.3 ± 0.3 | 6.2 ± 0.1 |
| MRT (h) | 0.583 ± 0.015 | 6.57 ± 3.26 | 1.91 ± 0.24 |
| $T_{1/2}$ (h) | 0.805 ± 0.298 | 5.35 ± 2.88 | 3.84 ± 3.47 |
| F (Bioavailability, %) | 100% | 6.7% | 31.7% |

Methods
Test Articles

ABT-301 capsule (50 mg/capsule), ABT-301 API powder were provided by Anbogen Therapeutics, Inc. The oral dose suspension was prepared in 1% (w/v) carboxymethylcellulose sodium/0.5% (v/v) Tween-80 in water (Water for Injection) to form a dosing suspension of 2 mg/mL. The IV formulation was prepared in polyethylene glycol 400/N,N-dimethylacetamide (DMA)/normal saline (30/5/65, w/v/v) to make the dosing solution at a final concentration of 1.5 mg/mL. The IV formulation was filtrated with 0.45 μM filter before injection.

Animal Experiment

Three males Beagle dogs were used in this study. Source of animals was form KITAYAMA LABES CO., LTD., Japan. All animals were housed in National Medical University. The humidity and temperature were well controlled as 50~75% and 20~25° C. The light and dark cycle was set as 12 h: 12 h. Drinking water were allowed ad libitum during housing. The experiments were designed as crossover study (three periods). Three males Beagle dogs were used for testing different dosage forms of ABT-301.

In period I, animals were administrated for ABT-301 oral capsule (2 capsules, 100 mg) via oral administration; In period II, animals were administrated for ABT-301 oral suspension (50 mL, 100 mg) via oral administration; In period III, animals were administrated for ABT-301 IV solution (10 mL, 15 mg) via intravenous injection.

The washout time was at least 144 hours between each period. Animals for oral administration were fasted overnight prior to dosing and 4 hours post-dose. In period I, animals were given 50 ml drinking water by oral gavage within 5 minutes after ABT-301 capsule dosing.

Sample Collection

Each blood samples (0.7~0.8 mL) was collected by cephalic vein and added in a 3 mL microcentrifuge tube containing anti-coagulant EDTA, followed by centrifugation (3,000 g) for 10 min. The plasma fraction was transferred to a clean 1.5 microcentrifuge tube and stored at −80° C. for further analysis. The sampling time points of period I and period II were set at pre-dose, 0.25, 0.5, 1, 2, 4, 6, 8, 12 and 24 h post dosing; The sampling time points of period I and period III were set at pre-dose, 0.083, 0.25, 0.5, 1, 2, 4, 6, 8 and 12 h post dosing.

Bioanalytical Method

The plasma concentrations of ABT-301 were determined by LC-MS/MS (LC-10AD$_{VP}$ pump, SIL-HT$_A$ autosampler, Shimadzu Corporation and API 4000 Triple Quadrupole mass spectrometer) method. The mobile phase consisted of acetonitrile/formic acid/water (46/1.0/54) at a flow rate of 1.0 mL/min into MS/MS. Separation was achieved on a Phenomenex, Luna, 5 μm, C18(2), 100 Å, 150×4.6 mm (Phenomenex, Inc., Taiwan). All quantitative analyzes were performed in the multiple reaction monitoring (MRM) mode. ABT-301 was analyzed in the positive mode with the monitoring ions at m/z 345.00 for parent ion and at m/z 326.90 for daughter ion. Internal standard (Cinacalcet, MW 357.41) was analyzed in the positive mode with the monitoring ions at m/z 357.70 for parent ion and at m/z 154.90 for daughter ion. The spray needle was 5500 V, desolvation temperature was 600° C., the declustering potential was 40 V and collision energy was 30 V.

Each of plasma samples (50 μL) was extracted with 200 μL of 100% CH3CN containing 0.2 ng/μL internal standard. After centrifuged, 200 μL of supernatant were evaporated to dryness and subsequently reconstituted with 200 μL of acetonitrile/formic acid/water mixture (40/0.1/60). Finally, an aliquot (50 μL) injected onto LC/MS/MS Pharmacokinetic Parameter Calculation Concentration of ABT-301 were analyzed by LC/MS/MS. Non-compartmental pharmacokinetic parameters analysis was provided, including plasma concentration-time data profile, elimination half-life ($T_{1/2}$) and mean residence time (MRT), maximum plasma concentration ($C_{max}$), time to peak concentration ($T_{max}$), the area under the concentration-time curve from time 0 extrapolated to infinity ($AUC_{(0-\infty)}$), area under the concentration-time curve from time 0 to the last measurable concentration ($AUC_{(0-t)}$), systemic clearance (CL or CL/F), volume of distribution (Vd or Vd/F) and bioavailability (F %) are calculated using Phoenix program. The equation of bioavailability (F %) was as follows:

F (%)=mean $AUC_{0-\infty}$(oral capsule or suspension)/ mean $AUC_{0-\infty}$ (IV solution).

Data of blood concentration and pharmacokinetic parameters of each individual animal and the "Mean±SD" of each group are reported.

In summary, the present crystalline forms of ABT-301 can exhibit unexpected stability and improved pharmacokinetic properties compared to other forms or salt thereof, thereby allowing said compound more suitable for drug development and satisfying the requirements for bioavailability and drug efficacy.

The specific embodiments of the present invention have been disclosed, but it is not intended to limit the present invention. Those with ordinary knowledge in the technical field to which the present invention belongs are capable of understanding. And in the case of deviating from the principle and spirit of the present invention, various changes and modifications can be made to it, so the scope of protection of the present invention should be based on those defined in the scope of the accompanying patent application.

What is claimed is:

1. A crystalline form of (E)-N-hydroxy-3-(1-(phenylsulfonyl) indolin-5-yl) acrylamide (ABT-301), wherein the crystalline form comprises Type A form or Type B form; wherein Type A form is characterized by an X-ray powder diffraction pattern comprising peaks at 2θ values of 9.6±0.2, 15.1±0.2, 15.7±0.2, 16.7±0.2, 18.4±0.2°, 19.0±0.2 and 20.4±0.2; and
   wherein Type B form is characterized by an X-ray powder diffraction pattern comprising peaks at 2θ values of 15.7±0.2, 16.6±0.2, 20.1±0.2 and 24.1±0.2.

2. The crystalline form of claim 1, wherein Type A form is characterized by an X-ray powder diffraction pattern further comprising peaks at 2θ value of 10.2±0.2°, 11.8±0.2, 17.4±0.2, 21.3±0.2 and 21.9±0.2.

3. The crystalline form of claim 1, wherein Type A form is hydrate.

4. The crystalline form of claim 1, wherein Type B form is characterized by an X-ray powder diffraction pattern further comprising peaks at 2θ value of 12.5±0.2° and 21.7±0.2°.

5. The crystalline form of claim 1, wherein Type B form is anhydrate.

6. The crystalline form of claim 1, having a melting point temperature of 125 to 132° C.

7. The crystalline form of claim 1, wherein Type A form has a TGA weight loss of 2 to 4% when heated to a temperature of 100 to 150° C.

8. The crystalline form of claim 1, wherein Type A form has a water uptake of 0.13 to 0.14% at 25° C./80% RH.

9. The crystalline form of claim 1, wherein Type B form has a TGA weight loss of 0.7 to 0.8% when heated to a temperature of 150 to 170° C.

10. The crystalline form of claim 1, wherein Type B form has a water uptake of 0.103 to 0.109% at 25° C./80% RH.

11. A pharmaceutical composition comprising the crystalline form of claim 1, a surfactant and an oil.

12. The pharmaceutical composition of claim 11, wherein the surfactant is polysorbate 80.

13. The pharmaceutical composition of claim 11, wherein the oil is castor oil.

14. The pharmaceutical composition of claim 11, which is a HDAC inhibitor.

15. The pharmaceutical composition of claim 11, which is in a form of a capsule.

16. The pharmaceutical composition of claim 15, comprising from 25 to 100 mg of the crystalline form.

17. The pharmaceutical composition of claim 15, which is encapsulated in a gelatin shell.

18. The pharmaceutical composition of claim 11, which further comprises a plasticizer.

19. The pharmaceutical composition of claim 18, wherein the plasticizer is propylene glycol.

20. A method of treating cancer or fibrosis, comprising administering to a patient in need thereof a therapeutically effective amount of the crystalline form of claim 1.

21. The method of claim 20, wherein the crystalline form of claim 1 is a HDAC inhibitor.

22. The method of claim 20, wherein the cancer is pancreatic cancer, bladder cancer, colorectal cancer, breast cancer, prostate cancer, renal cancer, hepatocellular cancer, lung cancer, non-small cell lung cancer (NSCLC), ovarian cancer, cervix cancer, gastric cancer, esophageal cancer, neuroendocrine cancer, bone cancer or head and neck cancer.

23. The method of claim 20, wherein the fibrosis is lung fibrosis, liver fibrosis, skin fibrosis or renal fibrosis.

* * * * *

UNITED STATES PATENT AND TRADEMARK OFFICE
CERTIFICATE OF CORRECTION

Page 1 of 1

PATENT NO. : 12,252,469 B2
APPLICATION NO. : 18/802914
DATED : March 11, 2025
INVENTOR(S) : Tsu-An Hsu et al.

It is certified that error appears in the above-identified patent and that said Letters Patent is hereby corrected as shown below:

On the Title Page

Change:
"(73) Assignees: Chuan Shih, Taipei (TW); ANBOGEN THERAPEUTICS INC., Taipei, TW"
To:
-- (73) Assignee: ANBOGEN THERAPEUTICS INC., Taipei (TW) --.

Signed and Sealed this
Fifteenth Day of July, 2025

Coke Morgan Stewart
*Acting Director of the United States Patent and Trademark Office*